(12) United States Patent
Frauenfeld

(10) Patent No.: US 9,884,128 B2
(45) Date of Patent: Feb. 6, 2018

(54) SALIPRO PARTICLES

(71) Applicant: Jens Frauenfeld, Stockholm (SE)

(72) Inventor: Jens Frauenfeld, Stockholm (SE)

( * ) Notice: Subject to any disclaimer, the term of this patent is extended or adjusted under 35 U.S.C. 154(b) by 0 days.

(21) Appl. No.: 14/649,095

(22) PCT Filed: Dec. 12, 2013

(86) PCT No.: PCT/EP2013/076404
§ 371 (c)(1),
(2) Date: Jun. 2, 2015

(87) PCT Pub. No.: WO2014/095576
PCT Pub. Date: Jun. 26, 2014

(65) Prior Publication Data
US 2016/0082125 A1  Mar. 24, 2016

(30) Foreign Application Priority Data

Dec. 18, 2012 (EP) .................................... 12197904

(51) Int. Cl.
A61K 9/14 (2006.01)
A61K 47/42 (2017.01)
(Continued)

(52) U.S. Cl.
CPC ...... A61K 47/48838 (2013.01); A61K 9/1274 (2013.01); A61K 9/1275 (2013.01);
(Continued)

(58) Field of Classification Search
CPC ........ A61K 9/141; A61K 9/145; A61K 9/146; A61K 9/1274; A61K 9/1275; A61K 47/06;
(Continued)

(56) References Cited

U.S. PATENT DOCUMENTS 5,652,339 A  7/1997 Lerch
7,083,958 B2  8/2006 Sligar
(Continued)

FOREIGN PATENT DOCUMENTS

WO  2004073684  11/2004
WO  2005039534  9/2005
(Continued)

OTHER PUBLICATIONS

Popovica et al., PNAS-US, 2012, 109(8),2908-2912.*
(Continued)

*Primary Examiner* — Jeffrey E. Russel
(74) *Attorney, Agent, or Firm* — Honigman Miller Schwartz and Cohn LLP; Fernando Alberdi; Jonathan P. O'Brien

(57) ABSTRACT

The invention provides a nanoscale particle comprising a lipid binding polypeptide, lipids and a hydrophobic agent, wherein the hydrophobic agent is different from the lipids, and wherein the lipid binding polypeptide is a saposin-like protein or a derivative or truncated form thereof. The invention further provides a process for preparing a particle comprising a saposin-like protein or a derivative or truncated form thereof and lipids comprising the step of (a) contacting the saposin-like protein or a derivative or truncated form thereof with solubilized lipids in a liquid environment and (b) allowing for the self-assembly of the particle at a pH of from 5.0 to 10.0. In addition, the invention provides a pharmaceutical composition comprising the particle of the invention for delivering a hydrophobic agent to an individual in need thereof and includes the use of the particle of the invention in preventing, treating or lessening the severity of a disease or its use in a diagnostic method, a cosmetic treatment, as hydrophobic agent delivery particle,
(Continued)

as a tool for drug development, drug screening, membrane protein research or as vaccination formulation.

27 Claims, 18 Drawing Sheets

(51) Int. Cl.

| | | |
|---|---|---|
| *A61K 47/48* | (2006.01) | |
| *A61K 47/62* | (2017.01) | |
| *A61K 47/69* | (2017.01) | |
| *A61K 9/127* | (2006.01) | |
| *A61K 47/24* | (2006.01) | |
| *A61K 38/16* | (2006.01) | |
| *A61K 47/54* | (2017.01) | |
| *A61K 47/64* | (2017.01) | |
| *A61K 39/00* | (2006.01) | |

(52) U.S. Cl.
CPC .............. *A61K 9/145* (2013.01); *A61K 9/146* (2013.01); *A61K 38/164* (2013.01); *A61K 47/24* (2013.01); *A61K 47/42* (2013.01); *A61K 47/543* (2017.08); *A61K 47/544* (2017.08); *A61K 47/62* (2017.08); *A61K 47/64* (2017.08); *A61K 47/6917* (2017.08); *A61K 47/6929* (2017.08); *A61K 39/00* (2013.01)

(58) Field of Classification Search
CPC .. A61K 47/08; A61K 47/44; A61K 47/48246; A61K 47/48876; A61K 47/48884; A61K 47/48892; A61K 38/1709; A61K 38/19; A61K 47/62; A61K 47/69; A61K 47/6929; C07K 14/47
See application file for complete search history.

(56) References Cited

U.S. PATENT DOCUMENTS

| | | | |
|---|---|---|---|
| 7,575,763 | B2 | 8/2009 | Sligar |
| 7,622,437 | B2 | 11/2009 | Morissey |
| 7,662,410 | B2 | 2/2010 | Sligar |
| 7,824,709 | B2 | 2/2010 | Ryan |
| 7,691,414 | B2 | 4/2010 | Sligar |
| 7,834,147 | B2 | 11/2010 | Qi |
| 2002/0177551 | A1 | 11/2002 | Terman |
| 2006/0057662 | A1 | 3/2006 | Sligar |
| 2007/0117179 | A1 | 5/2007 | Kudlicki |
| 2008/0248565 | A1 | 10/2008 | Katzen |
| 2009/0269373 | A1 | 1/2009 | Qi |
| 2009/0161828 | A1 | 6/2009 | Katzen |
| 2009/0257950 | A1 | 10/2009 | Sligar |
| 2010/0233782 | A1 | 9/2010 | Katzen |
| 2010/0311595 | A1 | 12/2010 | Ryan |
| 2011/0059159 | A1 | 3/2011 | Sakmar |
| 2011/0104781 | A1 | 5/2011 | Katzen |
| 2011/0195450 | A1 | 8/2011 | Kudlicki |
| 2011/0256224 | A1 | 10/2011 | Sigalov |
| 2012/0020878 | A1 | 1/2012 | Qi |
| 2012/0190609 | A1 | 7/2012 | Bader |
| 2016/0220664 | A1* | 8/2016 | Loving ................ A61K 39/21 |

FOREIGN PATENT DOCUMENTS

| | | |
|---|---|---|
| WO | 2005081743 | 5/2006 |
| WO | 2008051818 | 12/2008 |
| WO | 2010053489 | 5/2010 |
| WO | 2012154825 | 11/2012 |
| WO | WO 2012/154825 | * 11/2012 |

OTHER PUBLICATIONS

Popovic et al: "Structure of saposin A lipoprotein discs", PNAS vol. 109, No. 8, pp. 2908-2912 (Feb. 21, 2012).
Qi et al.: "Saposin C Coupled Lipid Nanovesicles Specifically Target Arthritic Mouse Joints for Optical Imaging of Disease Severity", Plos One vol. 7, No. 3, Mar. 2012, p. 33966.
Qi et al.: "Cancer-Selective Targeting and Cytotoxicity by Liposomal-Coupled Lysosomal Saposin C Protein", Clin Cancer Res, vol. 15, No. 18, 2009, pp. 5840-5851.
Bruhn: "A short guided tour through functional and structural features of saposin-like proteins" Biochem. J., vol. 389, No. 15, 2005, pp. 249-257.
Rossmann et al.: "Crystal Structures of Human Saposins C and D: Implications for Lipid Recognition and Membrane Interactions", Structure 16, 809-817, May 2008.
Ryan: "Nanodisks: hydrophobic drug delivery vehicles", Expert Opin Drug Deliv. Mar. 2008; vol. 5(3), pp. 343-351.
Ryan: "Nanobiotechnology applications of reconstituted high density lipoprotein", J Nanobiotechnology, Dec. 1, 2010; 8:28.
PCT/EP2013/076404 International Search Report dated Feb. 21, 2014.
Barral and Brenner, "CD1 antigen presentation: how it works", Nature Reviews Immunology, 7(12):929-941, 2007.
León et al., "Saposins utilize two strategies for lipid transfer and CD1 antigen presentation", Proceedings of the National Academy of Sciences, 109(12):4357-4364, 2012.
Winau et al., "Apoptotic Vesicles Crossprime CD8 T Cells and Protect against Tuberculosis", Immunity, 24:105-117, 2006.
Ciaffoni et al., "Saposin B binds and transfers phospholipids", The Journal of Lipid Research, 47(5):1045-1053, 2006.
Popovic et al., "Structure of saposin A lipoprotein discs", PNAS, 109(8):2908-2912, 2012.
Wu et al., "Single-particle cryoelectron microscopy analysis reveals the HIV-1 spike as a tripod structure", PNAS, 107(44):18844-18849, 2010.
International Search Report and Written Opinion dated Dec. 8, 2014 for related PCT Application No. PCT/EP2014/069512.
Chasman, D., "Protein Structure-Determination, Analysis, and Applications for Drug Discovery." Table 1, 2003.
Hersperger, "Insights into the Cytotoxic Potential of Human CD8+ T Cells: Implications for Virologic Control of HIV", University of Pennsylvania ScholarlyCommons, 2010, 24 pages.
Munford et al., "Saposin-like proteins (SAPLIP) carry out diverse functions on a common backbone structure", Journal of Lipid Research, 36:1653-1665, 1995.
U.S. Appl. No. 14/649,095, filed Jun. 2, 2015, Publication No. 2016/0082125.
U.S. Appl. No. 15/021,346, filed Mar. 11, 2016, Publication No. 2016/0220664.

* cited by examiner

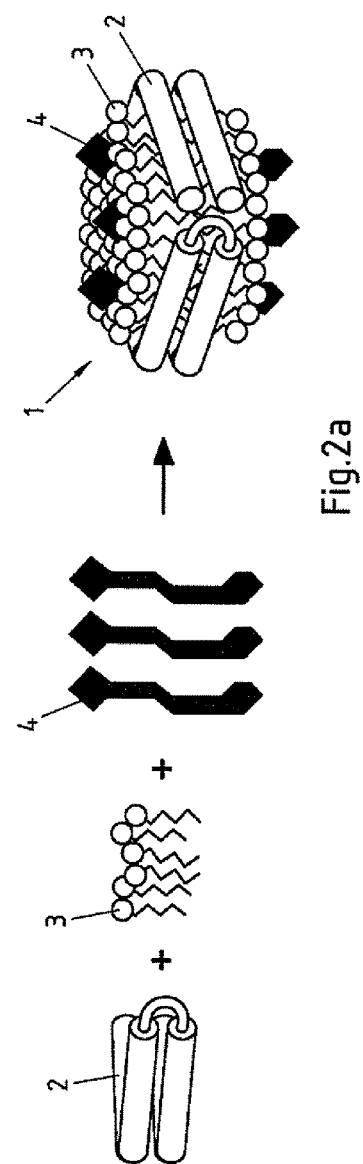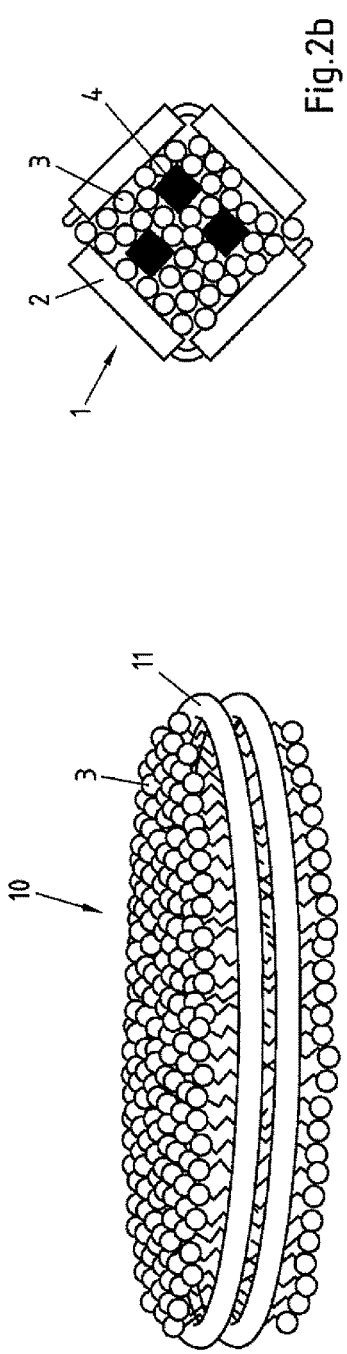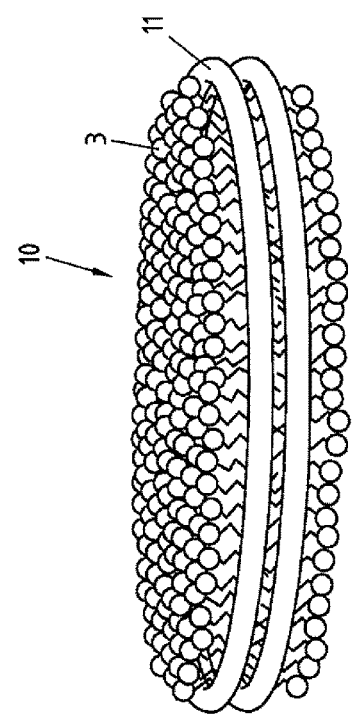

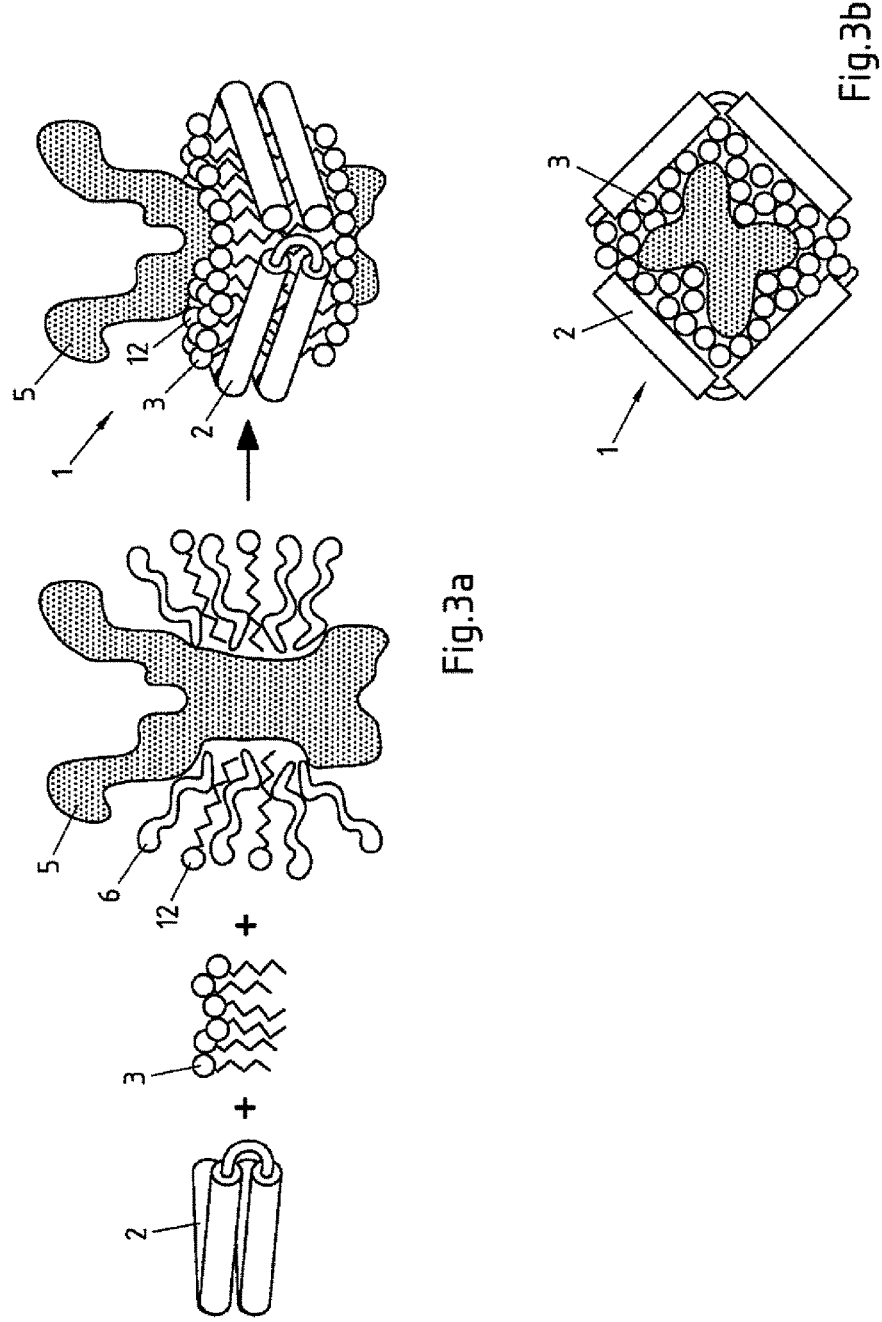

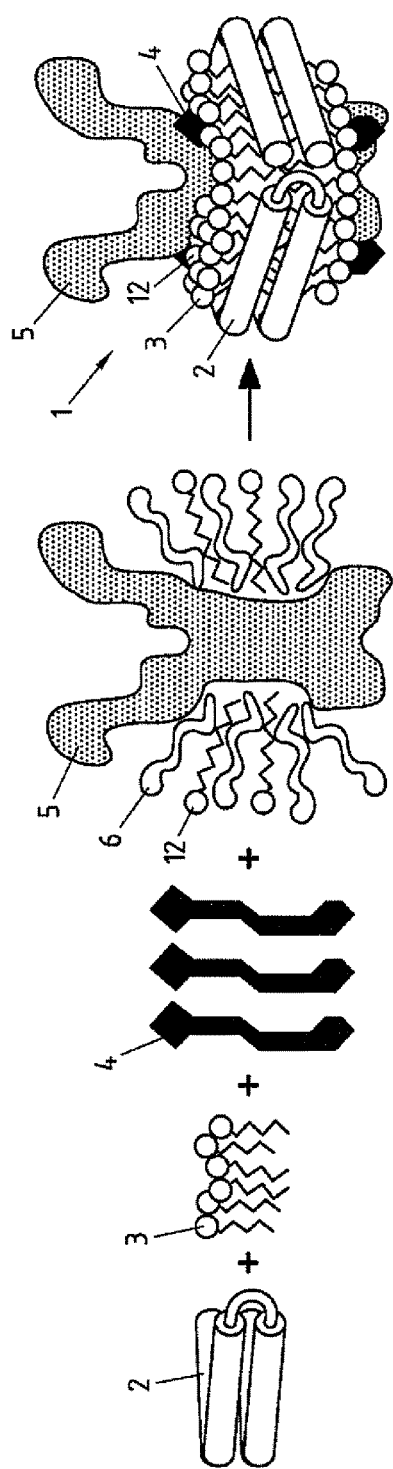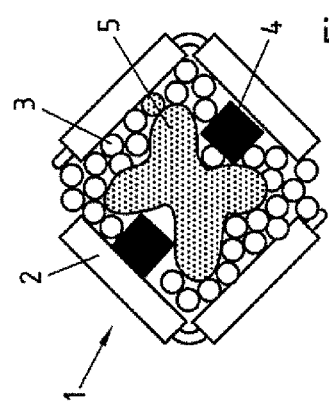
Fig.4a
Fig.4b

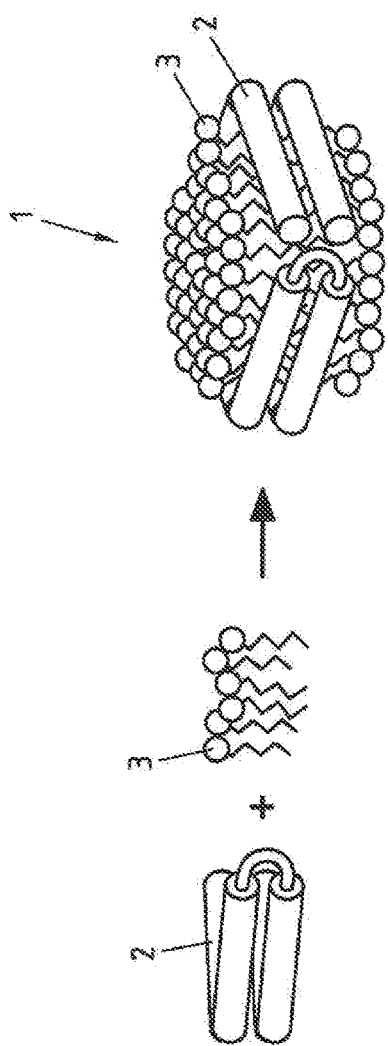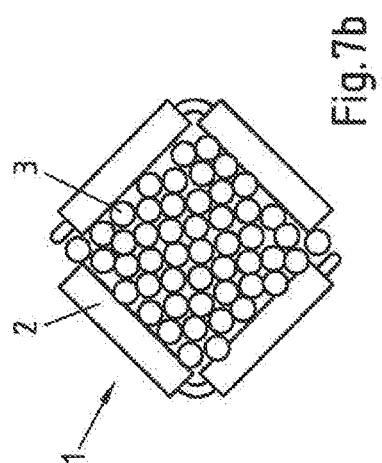

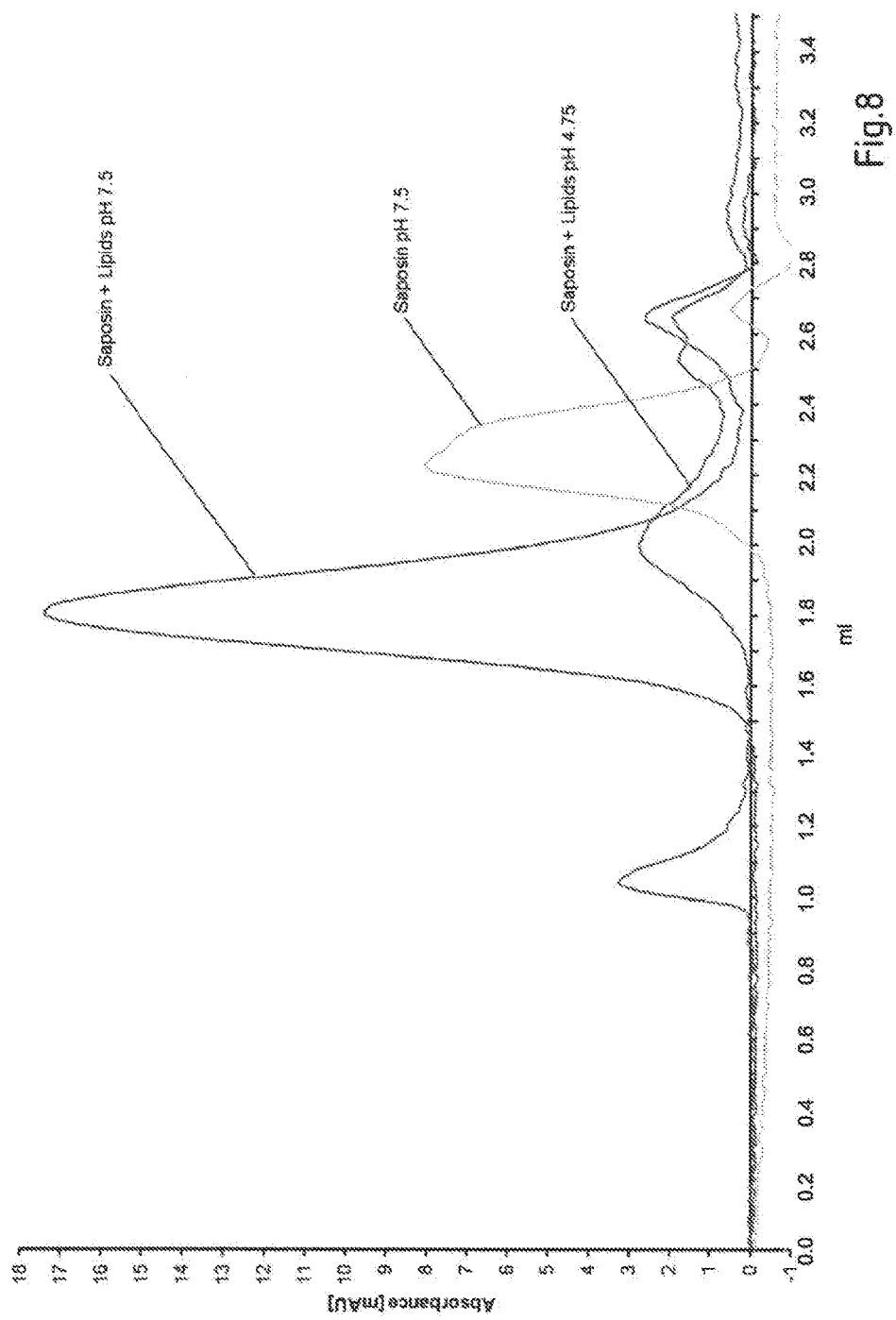

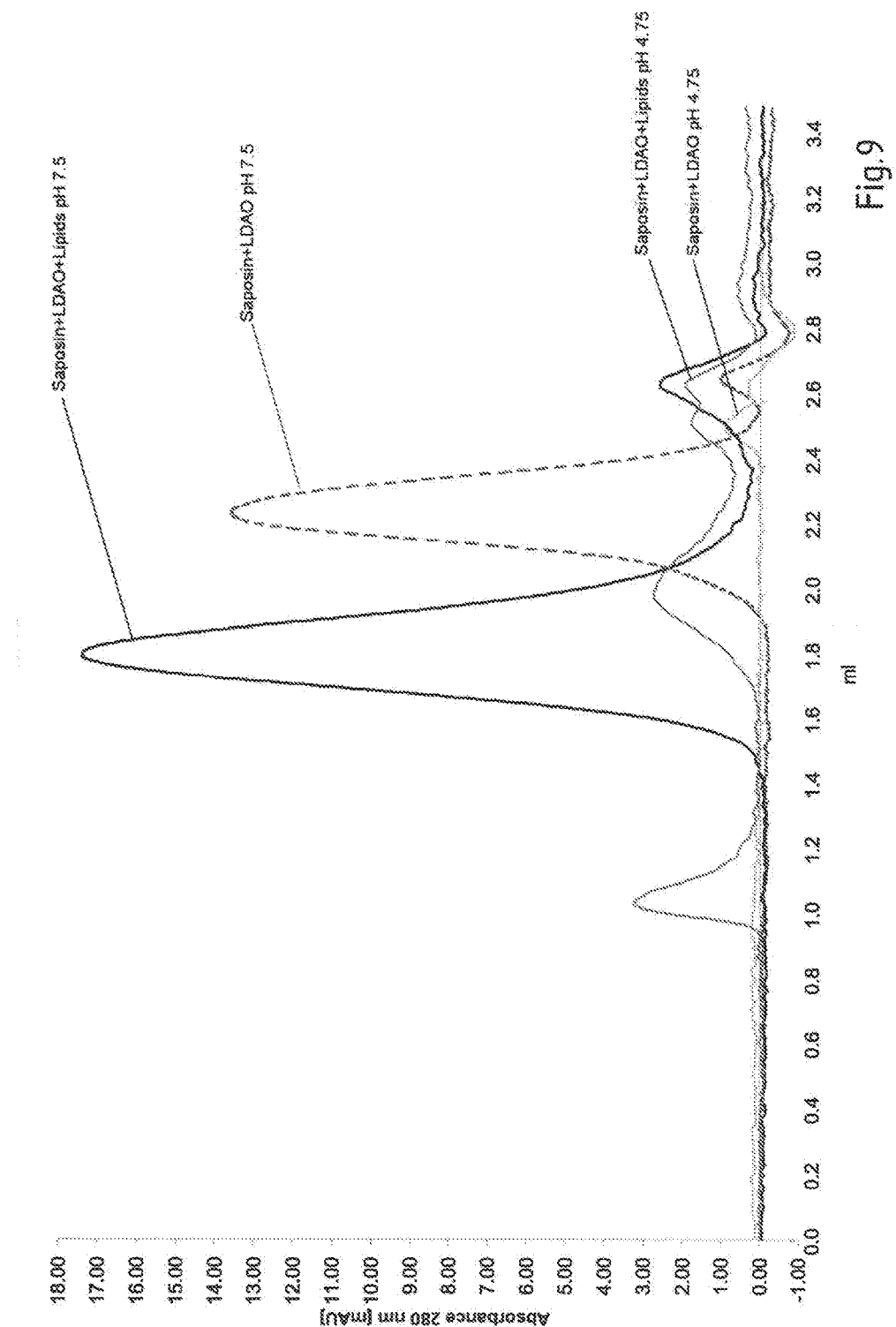

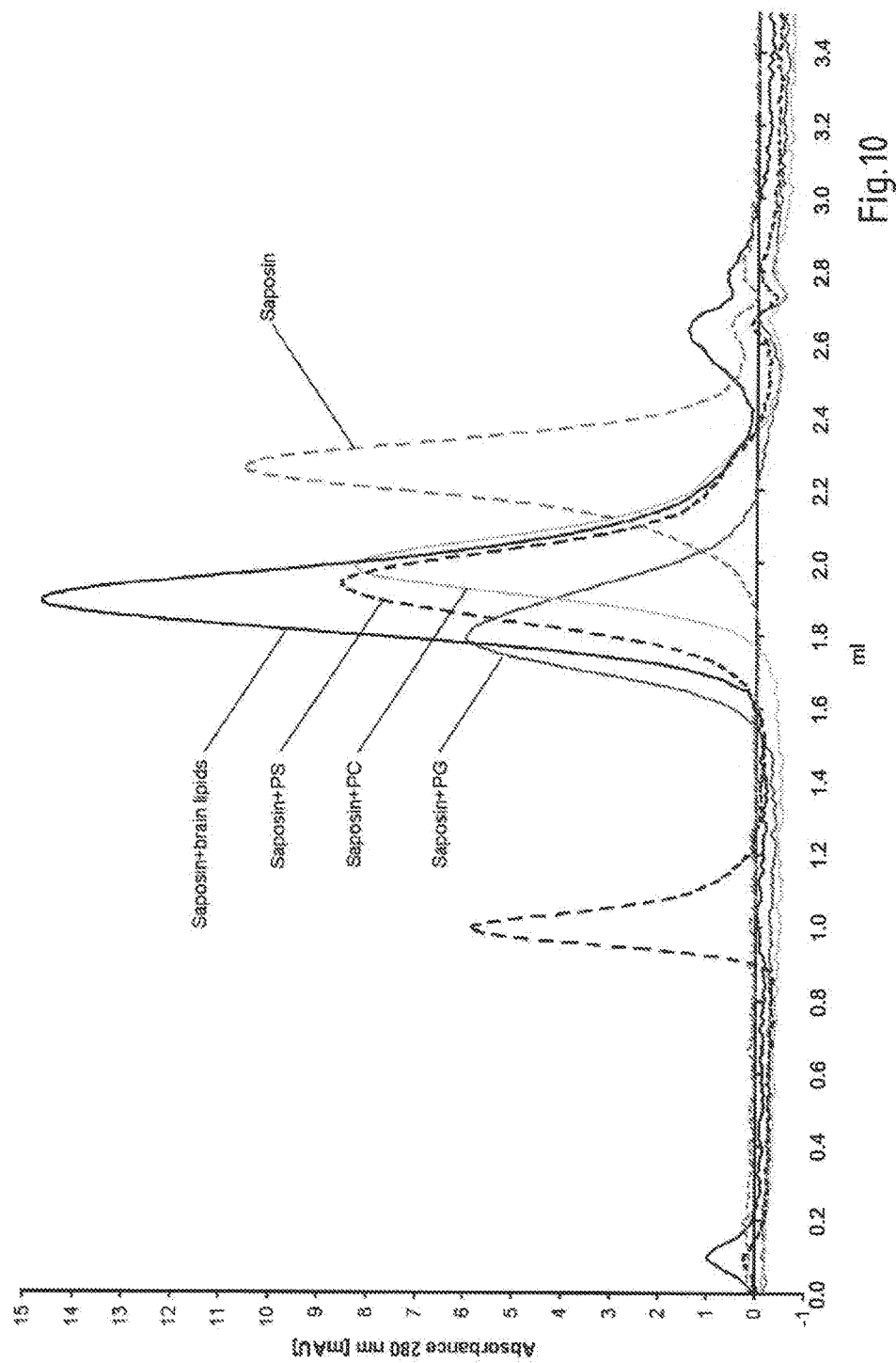

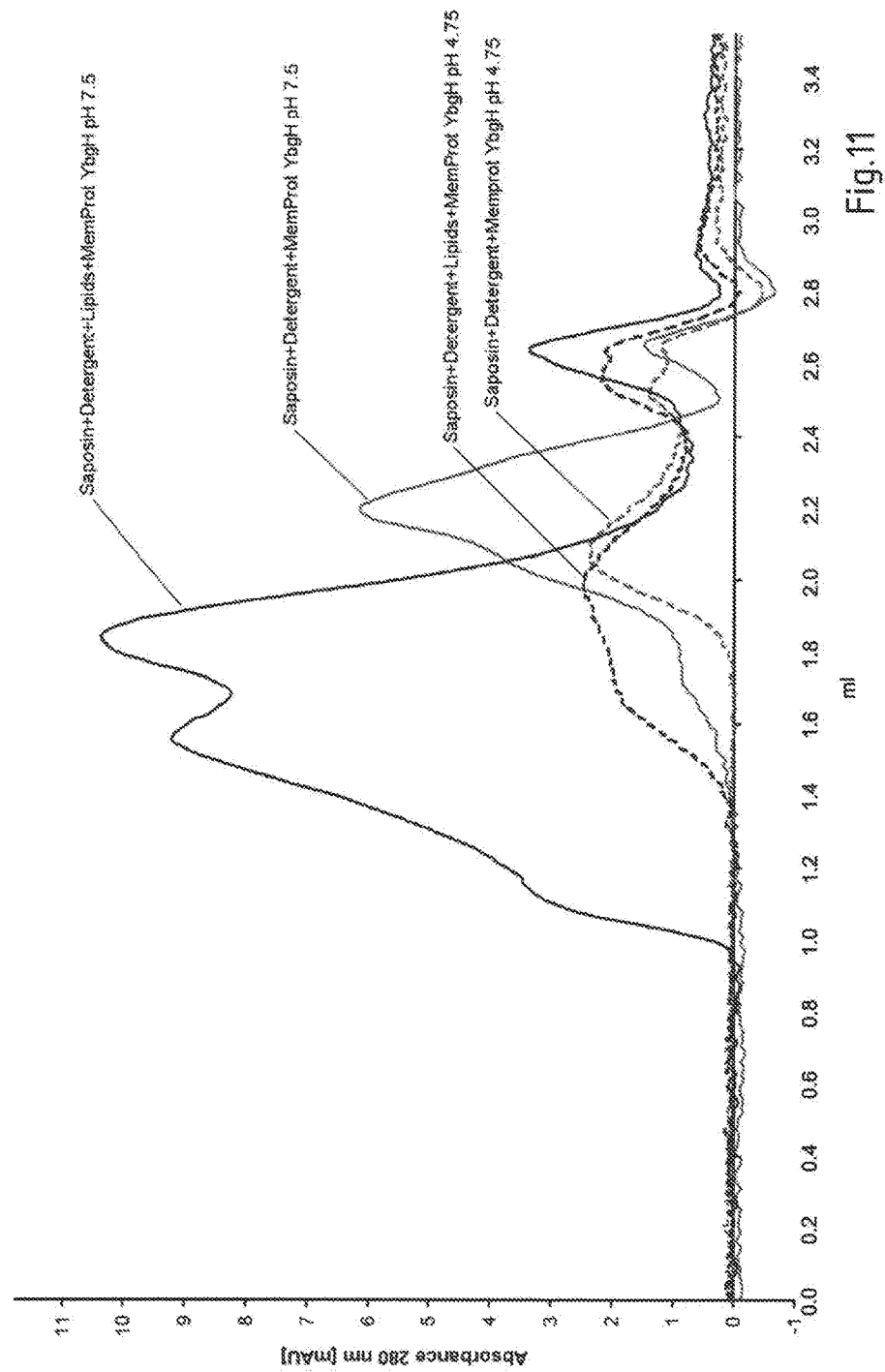

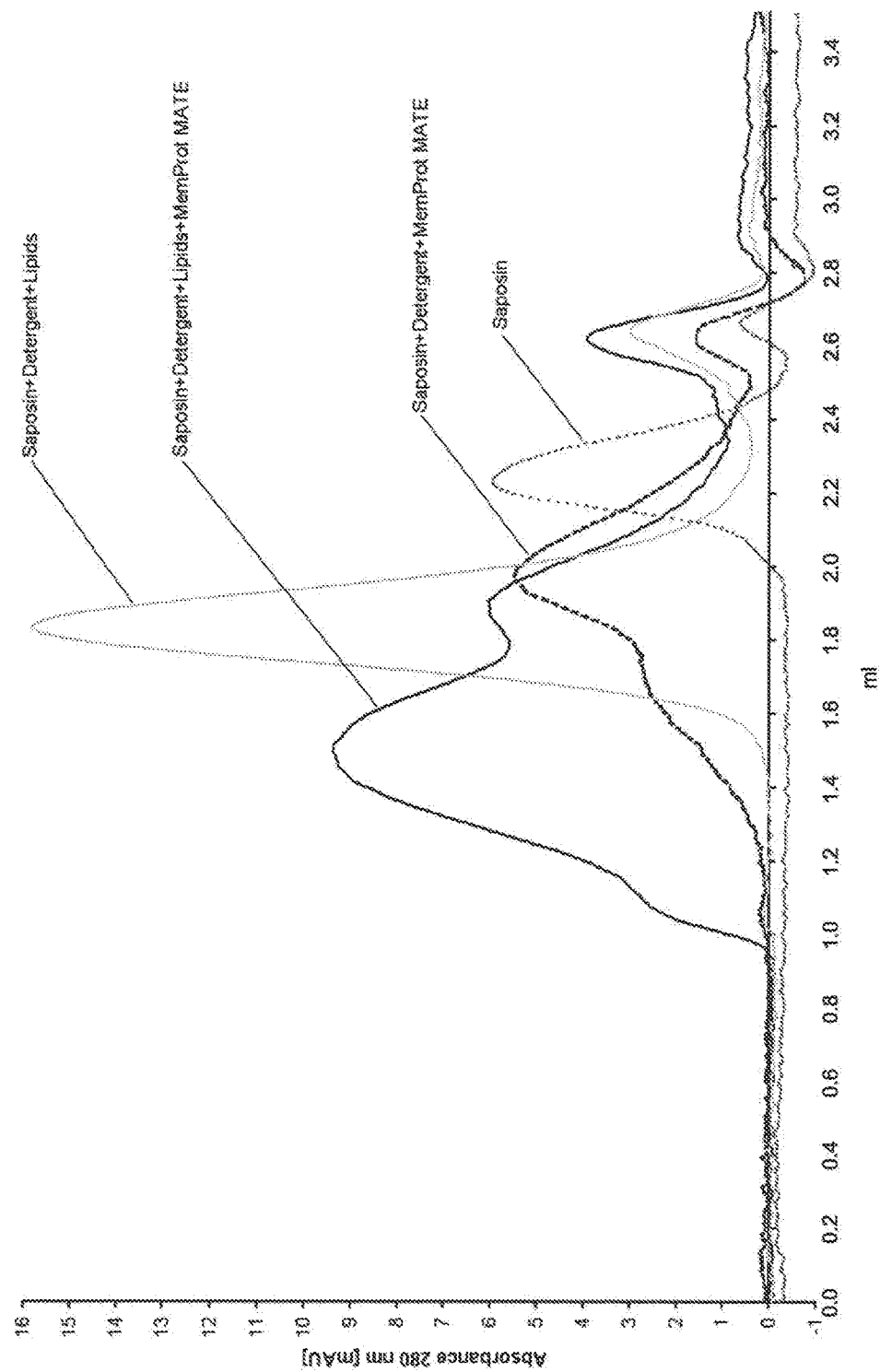

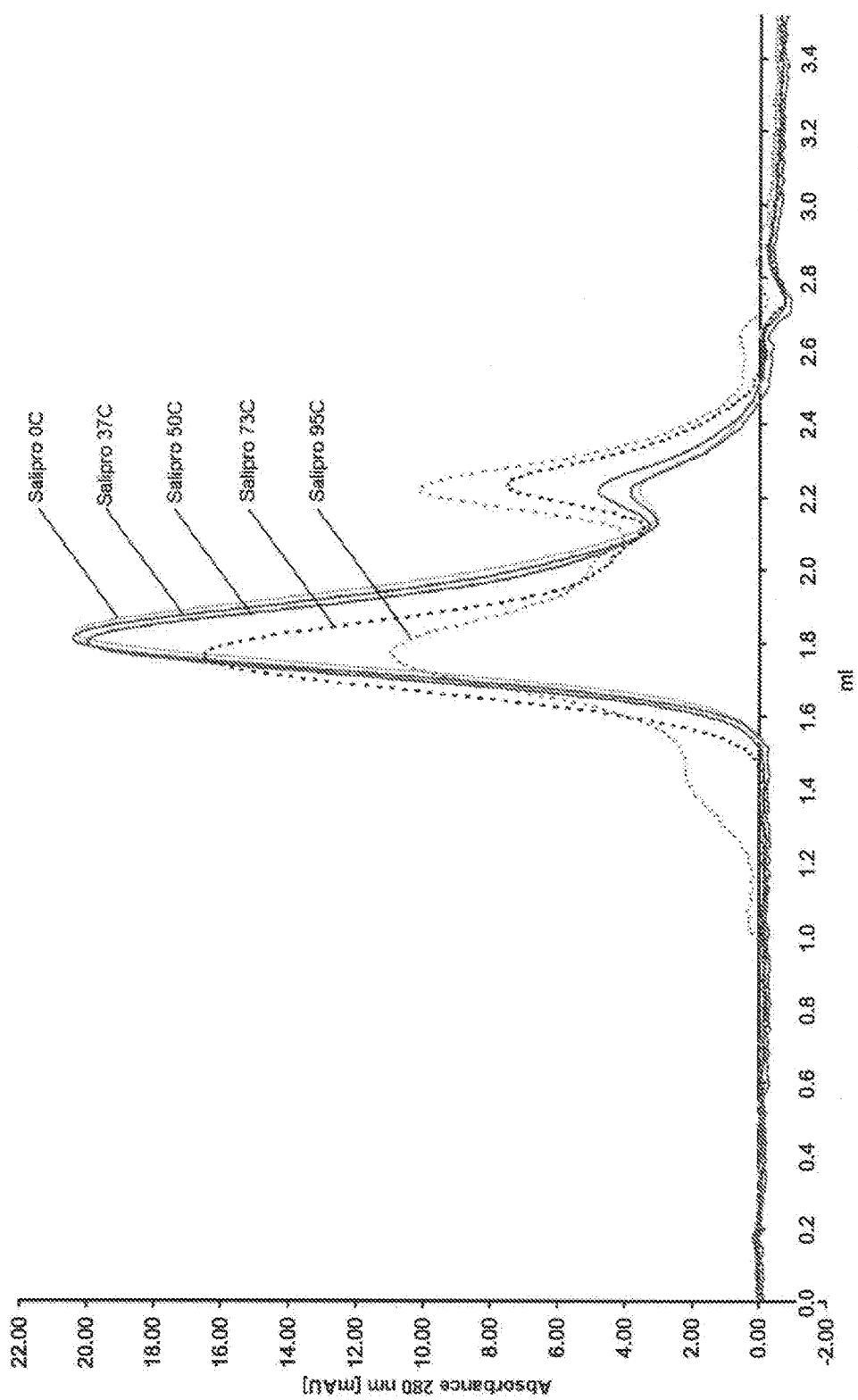

SALIPRO PARTICLES

CROSS-REFERENCE

This application claims priority under 35 U.S.C. § 371 to Patent Cooperation Treaty application PCT/EP2013/076404, filed Dec. 12, 2013, which claims the benefit of EP patent application no. 12197904.1, filed Dec. 18, 2012. This application incorporates by reference in its entirety, the disclosure of Patent Cooperation Treaty application PCT/EP2013/076404.

SEQUENCE LISTING

This application incorporates in its entirety the Sequence Listing entitled "2017-09-11_223265-371067_SEQ_LIST_ST25.txt", is 6,887 bytes in size and was created on Sep. 11, 2017, and filed electronically herewith.

TECHNICAL FIELD OF THE INVENTION

The invention relates to lipoprotein particles, their use as a delivery or carrier system for hydrophobic agents, such as hydrophobic drugs or membrane proteins, and to a process for the manufacture of such disc-like lipoproteins.

BACKGROUND OF THE INVENTION

Membrane proteins and hydrophobic compounds are notoriously difficult to handle and represent two of the major challenges for pharmaceutical or life-science research and applications: (i) rendering insoluble hydrophobic compounds or membrane proteins soluble in aqueous solutions and (ii) the administration of such hydrophobic matter as therapeutic and diagnostic agents.

Membrane proteins are encoded by approximately 30% of all ORF (Wallin and von Heijne, Protein Science 1998 April; 7 (4):1029-38) and represent an important class of drug targets since the majority of drugs, i.e. more than 60%, target in fact this class of proteins (Overington et al., Nature Reviews Drug Discovery 5, 993-996 (December 2006)). Membrane proteins play essential roles in many biological processes, such as signal transduction, transport of molecules and energy, recognition and cell-to-cell communication. Yet, membrane proteins are difficult to study due to their insolubility and tendency to aggregate when extracted from their natural lipid bilayer environment. In order to maintain the integrity of membrane proteins, an artificial hydrophobic environment is needed. Here, detergent micelles are most commonly employed which may, however, negatively impact on biocompatibility, can have adverse affects on membrane protein activity and may interfere with experimental conditions for assays.

Another major pharmacological challenge is represented by the administration and delivery of hydrophobic compounds and/or hydrophobic proteins as therapeutic or diagnostic agents. Due to the limited solubility of these hydrophobic agents, they are prone to aggregation, leading to locally highly concentrated drug particles that may cause high toxicity, unwanted immune responses and render the drug inactive (Allen and Cullis, SCIENCE, 303 (5665): 1818-1822, Mar. 19, 2004).

Therefore, applications that incorporate hydrophobic agents such as membrane proteins, drugs or diagnostic compounds into soluble particles are highly desired. Current methods that address these two challenges involve amongst others liposomes and reconstituted high-density lipoprotein (rHDL) particles (Chan and Boxer, Current Opinion in chemical Biology 11:1-7, 2007).

EP 1 596 828 B1 describes disc-shaped bioactive agent delivery particles comprising an apolipoprotein which tightly surrounds a lipid bilayer in a double belt-like fashion. The interior of said particles is formed by the hydrophobic region of the lipid bilayer. This is in contrast to liposomes, which are closed spherical bilayer shells containing an aqueous interior. The disc-shaped bioactive agent delivery particles described in EP 1 596 828 B1 have a Stokes diameter of about 10 nm and are proposed for use as delivery vehicles for hydrophobic pharmaceutical drugs such as amphotericin B or camptothecin.

EP 1 345 959 B1 describes a similar type of nanoscale particle with a diameter of about 10 nm and a height of about 5.5 nm. The particles are disc-shaped and composed of (i) an artificial membrane scaffold protein, (ii) a phospholipid bilayer and (iii) at least one hydrophobic or partially hydrophobic membrane protein. Said membrane scaffold protein again surrounds the lipid bilayer in a double belt-like fashion and is a derivative or a truncated form of human apolipoprotein A-1, lacks the N-terminal globular domain of human apolipoprotein A-1, is amphipathic and forms at least one α-helix and will, in aqueous environment, self-assemble with a phospholipid or mixture of phospholipids into a nanoscale particle of this discoidal shape. Such an engineered membrane scaffold protein (MSP) shall provide stability, size homogeneity and useful functionalities to the nanoscale discoidal lipoprotein particle.

However, there are several drawbacks with this currently available nanodisc technology in that, for example, a removal of detergent is required during assembly of the particles. Moreover, the size homogeneity provided by the tight double-belt like fit of the apolipoprotein-derived MSP seems to go at the expense of a fixed minimum particle size and a limitation as to the maximum diameters obtainable with the methods of the prior art.

The saposin-family comprises 4 small (~80 amino acids) proteins, saposin A to D, that bind and/or interact with lipids and function as essential cofactors for several lysosomal enzymes in sphingolipid catabolism (cf. Bruhn, Biochem J. (2005) 389, 249-257 and references cited therein). Saposins have been described to prefer negatively charged lipids and low pH, exhibiting markedly increased activities at acidic pH, with a pH optimum at the intra-lysosomal pH of 4.75. Saposin A, B, C, and D are proteolytically hydrolyzed from a single large precursor protein, prosaposin. The complete amino acid sequences for saposins A, B, C and D have been reported as well as the genomic organization and cDNA sequence of prosaposin (O'Brien et al. (1988) Science 241, 1098-1101; Furst et al (1992) Biochim Biophys Acta 1126: 1-16).

Saposin C is capable of inducing membrane fusion of phospholipid-containing vesicles in an acidic environment (Archives of Biochemistry and Biophysics 2003 Jul. 1; 415(1): 43-53), a feature not exhibited by the other saposins. Qi et al. (2009) *Clin Cancer Res* 15(18):5840-5851 report on saposin C-coupled dioleoylphosphatidylserine nanovesicles (SapC-DOPS) that contain an aqueous interior, have a mean diameter of about 190 nm and show tumor-targeting activity in vivo. In SapC-DOPS, saposin C or a peptide derived thereof acts as homing peptide for the liposome it is attached to. Saposin C then targets the liposome to cancer cells exposing phosphatidylserine on the outer leaflet of the cell membrane. The authors believe that a unique acidic microenvironment around cancer cells due to extracellular leakage of lysosomal enzymes makes tumor tissue an optimal target for saposin C. According to Qi et al., SapC-DOPS liposomes are prepared by drying solvent-dissolved phospholipids under $N_2$ (g), dispersing the dry phospholipids in acidic buffer (pH 5) containing purified saposin C, diluting the mixture 50× in a physiologic aqueous solution and facilitating nanovesicle assembly by subsequent sonication.

Popovic et al., PNAS, Vol. 109, No. 8 (2012) 2908-2912 report on the structure of saposin A detergent discs. Saposin A exists in a soluble and a lipid/detergent-bound state. In the absence of lipid, saposin A adopts a closed monomeric apo conformation. By contrast, the saposin A detergent disc structure reported by Popovic et al. reveals two chains of saposin A in an open conformation encapsulating 40 internally bound detergent molecules organized in a highly ordered bilayer-like hydrophobic core.

Besides the crystallization of saposin A detergent discs, Popovic et al. also describe the preparation of soluble lipid-saposin A complexes at pH 4.75 by a method requiring multiple steps. First, a uniform fraction of large unilamellar liposome vesicles is prepared by drying chloroform-dissolved lipids under $N_2$ (g), dispersing the dry lipids by vortex mixing in acidic buffer (50 mM sodium acetate pH 4.8, 150 mM NaCl), submitting the suspension to 10 cycles of freezing and thawing, blending in a vortex mixer for 5 min and extruding the mixture through a 200 nm filter. Mixing the thus prepared large unilamellar liposome vesicles with purified saposin A in acidic buffer resulted in soluble lipid-saposin A particles. The particle showed a narrow size distribution around an average hydrodynamic (Stokes) radius of 3.2 nm and contained about 5:1 lipid molecules per saposin A chain. The exact size of the particles was only moderately affected by the lipid to protein molar ratio and the composition of the liposomes. The authors observed similar 3.2 nm particles regardless of whether or not anionic phospholipids, cholesterol, or glycosphingolipids were present in the liposomal mixtures. In all cases, a single peak was observed in the size range of a Stokes radius of 3.2 nm, indicating a relatively narrow distribution of species. Hence, the technology of this publication is limited to a pH value of 4.75, to the aforementioned size of the particles, and includes a laborious upstream liposome preparation step.

Against this background, there is a need for a reliable and easy to perform method for generating stable, defined lipoprotein-particle compositions for the solubilization of membrane proteins and other hydrophobic compounds. This is particularly true in view of the elaborate and multi-step processes disclosed in the prior art for preparing discoidal lipoprotein particles.

A wide variety of hydrophobic agents could potentially benefit from the apolipoprotein- or saposin A-derived nanodisc technology described in the prior art. However, due to the 3.2 nm size limitation of the saposin A derived particles, it seems that—if at all—only small molecules may be incorporated into such particles at the acidic pH disclosed therein. Whereas bulky hydrophobic compounds and large biomolecules such as (oligomeric) membrane proteins can be incorporated into the Apolipoprotein A derived nanodiscs of the prior art, the maximum possible diameter is still limited by the double-belt like Apolipoprotein A perimeter of these particles. In addition, the 10 nm Apolipoprotein A derived nanodiscs may be too large for certain applications. Hence, there is a need for advanced nanodisc technology and superior liproprotein particles with flexible and controllable size ranges featuring the ability to adapt to the respective size of the hydrophobic agent that is to be incorporated into the lipoprotein particles. Such particles shall allow for simple integration of membrane proteins and other hydrophobic components which, for example, can be pharmaceutically or biologically active compounds or diagnostic compounds.

SUMMARY OF THE INVENTION

The problem underlying the invention is seen in the provision of nanoscale lipoprotein particles, the size of which can be controlled and/or the size of which adjusts to the nature of the incorporated molecules and which are easy to produce and maintain a uniform size, quality and composition over time.

This problem is solved by a particle comprising a lipid binding polypeptide, at least one kind of lipid and a hydrophobic agent, wherein the hydrophobic agent is different from the at least one kind of lipid, and wherein the lipid binding polypeptide is a saposin-like protein or a derivative or truncated form thereof.

The invention also provides a pharmaceutical or diagnostic composition that comprises the particles of the invention.

The invention further provides a process for the manufacture of particles comprising a lipid binding polypeptide and lipids, wherein the lipid binding polypeptide is a saposin-like protein or a derivative or truncated form thereof and wherein the process comprises the steps of contacting the lipid binding polypeptide with solubilized lipids in a liquid environment; and allowing for the self-assembly of the particle at a pH of from 5.0 to 10.

Finally, the particles of the invention can be used as a hydrophobic agent delivery vehicle, as a tool for drug development, drug screening, membrane protein research, and as a vaccination formulation.

Without being bound to this theory, it appears that the association of the hydrophobic agent with lipids and a saposin-like protein or a derivative or truncated form thereof provides a robust structure which is stable in aqueous solutions over a wide pH range, in particular at physiological pH, and allows larger particles than the 3.2 nm saposin A-derived lipoprotein particles of the prior art. Such particles are obtainable by the method of the invention which operates at a pH of from 5.0 to 10, thus allowing for self-assembly of the particles of the invention.

The saposin-like protein-lipoprotein particles obtainable by the method of the invention (designated "Salipro particles" herein) differ from the particles of the prior art in multiple features, for example by their inherent size flexibility and ability to adapt to the respective size of the hydrophobic agent that is to be incorporated into the lipoprotein particles.

Contrary to the expectation that saposin-lipoprotein particles should be best assembled at or close to the saposins' natural pH optimum of 4.75, it was found that saposin-lipoprotein particles with improved properties and an extended application spectrum can be obtained when a more neutral or basic pH is maintained during preparation of the particles. Surprisingly, it was found that at a pH of from 5.0 to 10 and in the presence of solubilized lipids, purified saposin-like protein or a derivative or truncated form thereof self-assembles into stable lipoprotein particles without the need of a laborious upstream liposome preparation step. This simple and reliable preparation method failed to yield satisfactory results when particle assembly was attempted at the saposins' natural pH optimum of 4.75 or in the absence of lipids.

The Salipro particles of the invention have proven to be capable of the incorporation of a variety of lipids, membrane proteins and hydrophobic compounds at a physiological pH, giving rise to nanoscale complexes that are soluble and stable in an aqueous environment.

The Salipro particles of the invention are robust over concentrating using standard centrifugal filter units, freezing and thawing. Moreover, practical experiments revealed that the Salipro particles of the invention display a certain degree of thermostability. In addition, it is possible to freeze-dry, store and re-hydrate the particles of the invention without any major quality deterioration observable.

DETAILED DESCRIPTION OF THE INVENTION

The lipid binding polypeptide is a saposin-like protein (SAPLIP) or a derivative or truncated form thereof. The term "saposin-like protein" (SAPLIP) as used herein is art-recognized and includes all members of the saposin-like protein (SAPLIP) family of lipid interacting proteins. The SAPLIP family is characterized by the saposin-fold, a conserved alpha-helical three-dimensional structure that is stabilized by highly conserved intramolecular disulphide bonds (Munford et al. (1995), Journal of Lipid Research, vol. 36, no. 8, 1653-1663 and Bruhn (2005), Biochem J 389 (15): 249-257). Examples of members of the saposin-like protein (SAPLIP) family according to the invention are described in Munford et al. (1995), Journal of Lipid Research, vol. 36, no. 8, 1653-1663 and Bruhn (2005), Biochem J 389 (15): 249-257, both of which disclosures are hereby incorporated by reference in their entirety.

In the ligand-free (i.e. detergent-free/lipid-free), "closed" state, the SAPLIPs adopt a monomeric compact four-helix bundle-type structure, the saposin fold. This fold is exemplified by the structure of the closed apo form of human saposin A (Protein Data Bank (PDB) ID code: 2DOB, Ahn et al. (2006) Protein Sci. 15: 1849-1857) or the structures of saposin C (PDB ID code: 1M12; de Alba et al. (2003) Biochemistry 42, 14729-14740), NK-lysin (PDB ID code: 1NKL; Liepinsh et al. (1997) Nat. Struct. Biol. 4, 793-795), amoebapore A (PDB ID code: 1OF9) and granulysin (PDB ID code: 1L9L; Anderson et al. (2003) J. Mol. Biol. 325, 355-365) which are all nearly identical and easily superimposable. SAPLIPs undergo a conformational change upon binding to ligands such as lipids or detergent molecules. In the ligand-bound "open" conformation, SAPLIPs adopt a V-shaped or boomerang-shaped conformation with exposed hydrophobic surfaces that contact the bound lipids. The open conformation is exemplified by the saposin A detergent disc structure of the prior art (PDB ID code: 4DDJ; Popovic et al., PNAS, Vol. 109, No. 8 (2012) 2908-2912) and the structure of saposin C bound to SDS detergent micelles (PDB ID code: 1SN6; Hawkins et al. (2005) J. Mol. Biol. 346: 1381-1392).

In the particles of the invention, the lipid binding polypeptide preferably is amphipathic, with one part of its structure more or less hydrophilic and facing the aqueous solvent and the other part more or less hydrophobic and facing the hydrophobic center of the particle which comprises the lipids. The lipid binding polypeptide is preferably characterized by amphipathic α-helices with more hydrophobic residues (such as A, C, F, G, I, L, M, V, W or Y) predominantly on one face of the helix and more polar or charged residues (such as D, E, N, Q, S, T, H, K, or R) on the other face of the helix.

The abbreviations for amino acid residues as used herein are as follows: A, Ala, alanine; V, Val, valine; L, Leu, leucine; I, lie, isoleucine; P, Pro, proline; F, Phe, phenylalanine; W, Trp, tryptophan; M, Met, methionine; G, Gly, glycine; S, Ser, serine; T, Thr, threonine; C, Cys, cysteine; Y, Tyr, tyrosine; N, Asn, asparagine; Q, Gln, glutamine; D, Asp, aspartic acid; E, Glu, glutamic acid; K, Lys, lysine; R, Arg, arginine; and H, His, histidine.

Contrary to the apolipoprotein-derived nanodiscs of the prior art, the lipid binding polypeptide of the invention does not enclose the lipids in a double belt-like fashion (cf. FIG. 1) but, rather, the particles of the invention are held together by a core comprising the lipids which is surrounded by two or more approximately V-shaped or boomerang-shaped lipid binding polypeptide arranged in a head-to-tail orientation with substantially no direct protein-protein contacts between the individual lipid binding polypeptides within a given particle of the invention (cf. FIGS. 2 to 7). Without wanting to be bound to this theory, it is believed that this arrangement of lipid binding polypeptides and lipids in the particles of the invention provides the size flexibility that is observed when bulky hydrophobic agents or increasing amounts of lipids are incorporated into the inventive particles.

Whereas the ability to interact with lipids as well as the above described amphipathic nature and three-dimensional structure is highly conserved among SAPLIPs, they are highly diverse on the amino acid sequence level, with sequence identities below the usual threshold zone of 25-30% identity to define homology (cf. sequence comparison in FIGS. 4A and 4B of Bruhn (2005), Biochem J 389 (15): 249-257, which figures are hereby specifically incorporated by reference).

In the lipoprotein particles of the invention, the lipid binding polypeptide serves primarily as a structural protein, providing the scaffold for the disc-like structure of the lipoprotein particles of the invention. For this reason, structural features, in particular the saposin-fold that is characteristic of the SAPLIPs, are more important for defining the lipid binding polypeptide of the invention as compared to mere sequence determinants.

Examples of SAPLIPs according to the invention are saposins A, B, C or D (for example from *Homo sapiens* [cf. SEQ ID NO. 1 to 4], *Equus caballus*, *Bos taurus*, *Mus musculus*, *Oryctolagus cuniculus*, *Rattus norvegicus* or *Xenopus laevis*); Surfactant protein B (for example from *Homo sapiens*, *Canis familiaris*, *Mus musculus*, *Oryctolagus cuniculus*, *Ovis aries* or *Rattus norvegicus*); Granulysin (for example from *Homo sapiens*; cf. SEQ ID NO. 5); NK-lysin (for example from *Sus scrofa*; cf. SEQ ID NO. 6); NK-lysin orthologues (for example from *Equus caballus* or *Bos taurus*); Amoebapores (for example from *Entamoeba histolytica*); Amoebapore orthologues (for example from *Entamoeba dispar* or *Entamoeba invadens*); Amoebapore-like protein (for example from *Fasciola hepatica*); Naegleriapores (for example from *Naegleria fowleri*); Clornorin (for example from *Clonorchis sinensis*); Prosaposin (for example from *Homo sapiens*, *Equus caballus*, *Bos taurus*, *Mus musculus*, *Oryctolagus cuniculus*, *Rattus norvegicus* or *Xenopus laevis*) and MSAP (for example from *Homo sapiens*).

The sequences of specific SAPLIPs used according to the invention are given in FIGS. 4A and 4B of Bruhn (2005), Biochem J 389 (15): 249-257, which figures and sequences specified therein are hereby specifically incorporated by reference. The sequences of particular SAPLIPs used according to the invention are given in the sequence listing as follows: SEQ ID NO. 1 Saposin A [*Homo sapiens*]; SEQ ID NO. 2 Saposin B [*Homo sapiens*]; SEQ ID NO. 3 Saposin C [*Homo sapiens*]; SEQ ID NO. 4 Saposin D [*Homo sapiens*]; SEQ ID NO. 5 Granulysin [*Homo sapiens*]; SEQ ID NO. 6 NK-lysin [*Sus scrofa*].

A SAPLIP used according to the invention may also be a polypeptide comprising the saposin-fold as part of a multi-domain protein. This is for example the case in acid sphingomyelinase (from *Homo sapiens, Caenorhabditis elegans, Ciona intestinalis, Anopheles, Drosophila, Mus musculus or Rattus norvegicus*); GDSL lipase such as acyloxy hydrolase (from *Homo sapiens*(Gly-Asp-Ser-Leu) (SEQ ID NO. 7) or *Rattus norvegicus* (Gly-Asp-Ser-Leu) (SEQ ID NO. 8)); Countin (from *Dictyostelium discoideum*); J3-crystallin (from Tripedalia cystophora) and Plant aspartic proteases (from Viridiplantae). A further SAPLIP used according to the invention can be bacteriocin AS-48. Bacteriocin AS-48 displays antimicrobial activity, is also able to bind lipids and possesses the same fold as the remaining SAPLIP family members but is devoid of any disulphide bridges.

Whereas, in the following, the invention is described in more detail for saposin A or a derivative or truncated from thereof as lipid binding polypeptide, and whereas saposin A or a derivative or truncated from thereof as lipid binding polypeptide is a preferred embodiment, the invention shall not be limited thereby. Rather, the invention explicitly extends to the entire family of saposin-like proteins (SAPLIPs) as lipid binding polypeptides of the invention. Due to the high degree of structural and functional conservation among SAPLIPs, the features and advantages of certain embodiments of the invention with saposin A as lipid binding polypeptide are expected to also apply to other embodiments using other SAPLIPs or derivatives or truncated forms thereof as lipid binding polypeptide of the invention.

According to a preferred embodiment, the SAPLIP is saposin A, B, C or D, in particular a saposin selected from (*Homo sapiens, Equus caballus, Bos taurus, Mus musculus, Oryctolagus cuniculus, Rattus norvegicus or Xenopus laevis*) saposin A, saposin B, saposin C or saposin D. In one embodiment, the SAPLIP is (*Homo sapiens, Equus caballus, Bos taurus, Mus musculus, Oryctolagus cuniculus, Rattus norvegicus or Xenopus laevis*) saposin A, saposin B or saposin D.

Saposin C is special among the saposins in that it is capable of inducing membrane fusion, a feature which is not exhibited by the other saposins. The membrane fusion activity may not always be desirable. According to a particular embodiment of the invention the lipid binding polypeptide is a saposin-like protein (SAPLIP) or a derivative or truncated form thereof, provided that the SAPLIP is not saposin C or provided that the SAPLIP is not saposin C or a derivative or truncated form thereof.

In one embodiment, the SAPLIP is of human origin (i.e. a *Homo sapiens* SAPLIP).

In a preferred embodiment, the SAPLIP is saposin A, preferably (*Homo sapiens, Equus caballus, Bos taurus, Mus musculus, Oryctolagus cuniculus, Rattus norvegicus or Xenopus laevis*) saposin A, and particularly preferred human saposin A, the amino acid sequence of which is given as SEQ ID NO. 1. Saposin A is a known protein. Its expression, purification and crystallization as LDAO-detergent complex is for example, described in PNAS, Vol. 109, No. 8 (2012) 2908-2912 (Popovic et al.).

According to one embodiment of the invention, the lipid binding polypeptide comprises the full length sequence of a SAPLIP. In another embodiment, the lipid binding polypeptide is a derivative of a SAPLIP, in particular a polypeptide comprising an amino acid sequence with at least 20, 30, 40, 50 or 60%, preferably at least 75% identity to the full length sequence of the respective SAPLIP. In particular, the lipid binding polypeptide can comprise a sequence having an identity with the full length sequence of a SAPLIP of at least 80%, 85%, 90% or 95%.

The term "Sequence identity" as used herein refers to a degree of identity between proteins that can be calculated by optimal alignment of the sequences using a scoring matrix such as the Blosum62 matrix described in Henikoff S. and Henikoff J G., P. N. A. S. USA 1992, 89: 10915-10919. Calculation of the percentage identity and optimal alignment of two sequences using the Blosum62 similarity matrix and the algorithm of Needleman and Wunsch (J. Mol. Biol. 1970, 48: 443-453) can be performed using the GAP program of the Genetics Computer Group (GCG, Madison, Wis., USA) using the default parameters of the program.

As a comparison for amino acid alignments the EMBL-online tool "EMBOSS Stretcher" (ebi.ac.uk/Tools/psa/emboss_stretcher) is used, using the programs default settings.

In another embodiment, the derivative of a SAPLIP is a polypeptide comprising a sequence having one or more amino acid deletions, additions, insertions and/or substitutions in the amino acid sequence of the respective SAPLIP. For example, the SAPLIP derivative can be a polypeptide comprising a sequence of a particular SAPLIP in which 1 to 40, preferably 1 to 30, and in particular 1 to 20 or 1 to 15 amino acids have been deleted, added, inserted and/or substituted.

The term "deletion" as used herein refers to the removal of 1, 2, 3, 4, 5 or more amino acid residues from the respective starting sequence.

The term "insertion" or "addition" as used herein refers to the insertion or addition of 1, 2, 3, 4, 5 or more amino acid residues to the respective starting sequence.

The term "substitution" as used herein refers to the exchange of an amino acid residue located at a certain position for a different one.

According to another embodiment of the invention, the lipid binding polypeptide is a derivative of saposin A that comprises one or more fragments of SEQ ID NO. 1. Preferred fragments correspond to the helices α1, α2, α3 and α4 of saposin A, wherein helix α1 is formed by the following continuous stretch of amino acids: "SLPCDICKDV-VTAAGDMLK" (SEQ ID NO. 9); helix α2 is formed by the following continuous stretch of amino acids: "ATEEEILVYLEKTCDWL" (SEQ ID NO. 10); helix α3 is formed by the following continuous stretch of amino acids: "PNMSASCKEIVDSYLPVILDIIKGEMS" (SEQ ID NO. 11); and helix α4 is formed by the following continuous stretch of amino acids: "PGEVCSAL" (SEQ ID NO. 12). According to a particular embodiment of the invention, the derivative of saposin A is a polypeptide comprising a sequence selected from helices α1, α2, α3, α4 of saposin A and combinations thereof, in particular wherein the polypeptide comprises the sequences of helices α1, α2 and α3 of saposin A. The fragments of saposin A, such as its helices α1, α2, α3, α4, may have one or more amino acid deletions, additions, insertions and/or substitutions in the amino acid sequence.

When a derivative or truncated form of saposin A is used as lipid binding polypeptide according to the invention, said derivative or truncated form should be amphipathic, form at least one alpha helix, and be capable of self-assembling together with solubilized lipids into lipoprotein particles when employed in the preparation process according to the invention which is described in detail below. As used herein, the term "amphipathic" refers to polypeptides or molecules having both hydrophilic and hydrophobic regions.

Preferably, if a derivative of a SAPLIP is used, the six cysteine residues corresponding to the six cysteines in the SAPLIP founding member saposin A should be present. It is referred in this respect to the positions of the cysteines in the sequence comparison in FIGS. 4A and 4B of Bruhn (2005), Biochem J 389 (15): 249-257, which figures are hereby specifically incorporated by reference.

The lipid binding polypeptide according to the invention may also include one or more non-natural amino acids; amino acid analogs, or a peptidomimetic structure, in which the peptide bond is replaced by a structure more resistant to metabolic degradation.

According to another embodiment of the invention the lipid binding polypeptide comprises additionally a tag such as a His6-tag, Strep-tag, Avi-tag, Myc-tag, Gst-tag, JS-tag, cysteine-tag, FLAG-tag or other tags known in the art at the N-terminus or at the C-terminus.

The lipid binding polypeptide of the invention can also be a chimeric polypeptide. As used herein, "chimeric" refers to two or more molecules that are capable of existing separately and are joined together to form a single molecule having the desired functionality of all of its constituent molecules. The constituent molecules of a chimeric molecule may be joined synthetically by chemical conjugation or, where the constituent molecules are all polypeptides or analogs thereof, polynucleotides encoding the polypeptides may be fused together recombinantly such that a single continuous polypeptide is expressed. Such a chimeric molecule is also known as "fusion protein". The various constituents of the chimeric polypeptide can be directly attached to each other or can be coupled through one or more linkers.

In one embodiment, the lipid binding polypeptide is a chimeric polypeptide further comprising a functional moiety such as a targeting moiety or a bioactive moiety.

When the particles of the invention are used as drug delivery vehicles, such a targeting moiety can, for example, serve to target the particles of the invention to a particular cell or tissue type, or to the infectious agent itself. In some embodiments, the particle includes a targeting moiety attached to a lipid binding polypeptide or lipid component. In some embodiments, the hydrophobic agent that is incorporated into the particle has a targeting capability. The targeting moiety can for example have receptor recognition properties so that the particles can be targeted to a specific cell surface receptor. For example, the particles of the invention may be targeted to a particular cell type known to harbor a particular type of infectious agent, for example by modifying the lipid binding polypeptide component of the particles to render it capable of interacting with a receptor on the surface of the cell type being targeted. In one embodiment, the targeting moiety is selected from the group consisting of natural or synthetic ligands, antibodies and antibody fragments or other biomolecules suitable for targeting purposes.

When the lipid binding polypeptide comprises a bioactive moiety, this can be selected, for example, from a drug, a cytotoxic agent, an enzyme, a label, a fluorophore, a contrast agent and a radiolabel.

Suitable lipids for the purpose of the invention can be selected from naturally occurring lipids, synthetic lipids, modified lipids, fats, waxes, sterols, fat-soluble vitamins, monoglycerides, diglycerides, triglycerides, phospholipids, fatty acids, glycerolipids, glycerophospholipids, sphingolipids, saccharolipids, polyketides, sterol lipids and prenol lipids or combinations thereof.

The term "lipid" as used herein is art-recognized and refers to a substance of biological or synthetic origin that is soluble or partially soluble in organic solvents or which partitions into a hydrophobic environment when present in aqueous phase.

The term "lipid" as used herein is not meant as a single lipid molecule in the particle of the invention. In fact, it is meant as a plurality of the same lipid molecules or a plurality of at least two different kinds of lipid molecules being present therein.

According to a preferred embodiment, the lipids are lipid bilayer forming lipids and/or biocompatible lipids.

The term "biocompatible" as used herein denotes being biologically compatible by not producing a toxic, injurious, or immunological response in living tissue.

As used herein, "bilayer-forming lipid" refers to a lipid that is capable of forming a lipid bilayer with a hydrophobic interior and a hydrophilic exterior. Any bilayer-forming lipid that is capable of associating with a SAPLIP or a derivative or truncated form thereof to assemble into a disc-shaped structure may be used in accordance with the invention. Bilayer-forming lipids include, but are not limited to, phospholipids, sphingolipids, glycolipids, alkylphospholipids, ether lipids, and plasmalogens. One type of bilayer-forming lipid may be used or a mixture of two or more types.

Particles may also include lipids that are not bilayer-forming lipids. Such lipids include, but are not limited to, cholesterol, cardiolipin, phosphatidylethanolamine (this lipid may form bilayers under certain circumstances), oxysterols, plant sterols, ergosterol, sitosterol, cationic lipids, cerebrosides, sphingosine, ceramide, diacylglycerol, monoacylglycerol, triacylglycerol, gangliosides, ether lipids, alkylphospholipids, plasmalogens, prostaglandins, and lysophospholipids.

According to a preferred embodiment, the lipids are eukaryotic lipids and/or lipids present in the white and grey matter of the brain. Preferred lipids, for example, are phospholipids, glycosphingolipids, sterols, phosphatidylcholine, phosphatidylserine (PS), 2-oleoyl-1-pamlitoyl-sn-glycero-3-phosphocholine (POPC), 2-oleoyl-1-pamlitoyl-sn-glycero-3-glycerol (POPG), 2-oleoyl-1-pamlitoyl-sn-glycero-3-phosphoethanolamine (POPE), diacylglycerol, cholesterol, sphingomyelin, galactosylceramide, gangliosides, phosphatidylinositoles and sulphogalactoceramides or combinations thereof. Preferred lipids are eukaryotic lipids. Phosphatidylserine (PS) is a particularly preferred lipid.

In one embodiment, the lipids comprise or consist of phospholipids. Examples of suitable phospholipids include, but are not limited to, DMPC, DMPG, POPC, dipalmitoyl-phosphatidylcholine (DPPC), dipalmitoylphosphatidylserine (DPPS), cardiolipin, dipalmitoylphosphatidylglycerol (DPPG), distearoylphosphatidylglycerol (DSPG), egg yolk phosphatidylcholine (egg PC), soy bean phosphatidylcholine, phosphatidylinositol, phosphatidic acid, sphingomyelin, and cationic phospholipids.

In some embodiments, a lipid comprised in the particle of the invention may be a modified lipid including one or more bound functional moieties, such as a targeting moiety or a bioactive moiety as described above.

The term "detergent" as used herein is art-recognized and not comprised in the definition of "lipids" as used herein.

While many lipids have a similarly amphiphilic general structure as compared to detergents, i.e. a polar hydrophilic head group and a nonpolar hydrophobic tail—lipids differ from detergents in the shape of the monomers, in the type of aggregates formed in solution, and in the concentration range required for aggregation. Lipids are generally substantially cylindrical in structure; the volume occupied by the hydrophobic tail is similar to the volume occupied by the polar head group. Detergents monomers are generally more cone-shaped; the volume occupied by the hydrophobic tail is smaller than the volume occupied by the polar head group. Detergents tend to aggregate into spherical or ellipsoid micelles that are water soluble without forming bilayer structures in the absence of lipids (cf. handbook "Detergents and their uses in membrane protein science" from Anatrace, www.anatrace.com).

Examples of compounds comprised in the term "detergent" as used herein include anionic detergents such as alkylbenzenesulfonates or bile acids, cationic detergents and non-ionic or zwitterionic detergents such as lauryl-dimethyl amine-oxides (LDAO), Fos-Cholines, CHAPS/CHAPSO, alkyl glycosides such as short, medium or longer chain alkyl maltosides and glucosides.

The particles of the invention further comprise a hydrophobic agent that is different from the lipids otherwise comprised in the particle. This means that if the hydrophobic agent is itself a lipid or a modified lipid, the majority of lipids comprised in the particle (i.e. greater 50 mol-% based on the total amount of lipids present in the particle) should be different from the lipid that forms the hydrophobic agent. In one embodiment of the invention, the hydrophobic agent is not a lipid; in another embodiment of the invention, the hydrophobic agent is neither a lipid nor a detergent.

The hydrophobic agent that can be incorporated into the particles of the invention can be a hydrophobic organic compound and/or a hydrophobic biomolecule. It can be a therapeutically or biologically active hydrophobic agent or a hydrophobic agent which simply stabilizes the discoidal shape of the particle of the invention. A hydrophobic agent is an agent, i.e. a compound and/or a biomolecule, which does not fully penetrate into or remain soluble in water and/or which tends to aggregate and/or partition into a hydrophobic environment when present in aqueous phase. By being comprised in the particle of the invention, the hydrophobic agent is effectively solubilized in the hydrophobic interior of the particle. Thereby it can maintain its native functionalities such as e.g. catalytic activity or ligand binding.

Hydrophobic agents comprised in the particles of the invention generally include at least one hydrophobic (e. g. lipophilic) region capable of associating with or integrating into the hydrophobic portion of a lipid bilayer. As such the hydrophobic agent can also be a chimeric molecule, wherein a hydrophobic (e. g. lipophilic) moiety, module or compound capable of associating with or integrating into the hydrophobic portion of a lipid bilayer has been attached to another molecule. For example, a lipid- or fatty acid-coupled compound, especially a lipid- or fatty acid-coupled drug, can be used as hydrophobic agent according to this invention. In these cases, the compound or drug itself must not necessarily be hydrophobic. In some embodiments, at least a portion of the hydrophobic agent is intercalated between or penetrates into the hydrophobic portions (e.g. fatty acyl chains) of the lipid molecules in the interior of the particle.

The hydrophobic agent can, for example, be a biologically active agent, a drug, an active ingredient of a drug, an active ingredient of a cosmetic product, an active ingredient of a plant protective product, a dietary and/or nutritional supplement, a diagnostic probe, a contrast agent, a label and/or an indicator.

Hydrophobic drugs which can be included in the particle of the invention and administered to a patient in need thereof may be any drugs having low solubility in an aqueous environment. The low solubility in aqueous environment may only be apparent under certain conditions, e.g. certain pH or temperature ranges or when the concentration of the hydrophobic agent exceeds a certain threshold.

Drugs which, for example, can be included in the particle of the invention and administered to a patient in need thereof are such for the treatment of cancer, inflammatory or infective conditions, cardiovascular diseases, neurological disorders and rheumatism among others. The hydrophobic agent can be an anti-oxidant, a vitamin, an anti-proliferative agent, a hormone, a steroid, or an enzyme. It can be an herbicidal or a fungicidal compound.

Some specific examples of hydrophobic drugs that can be incorporated into the particles of the invention include: curcumin, sulfonamide, such as sulfonamide, sulfamethoxazole and sulfacetamide; trimethoprim, particularly in combination with sulfamethoxazole; a quinoline such as norfloxacin and ciprofloxacin; a beta-lactam compound including a penicillin such as penicillin G, penicillin V, ampicillin, amoxicillin, and piperacillin, a cephalosporin such as cephalosporin C, cephalothin, cefoxitin and ceftazidime, other beta-lactam antibiotics such as imipenem, and aztreonam; a beta lactamase inhibitor such as clavulanic acid; an aminoglycoside such as gentamycin, amikacin, tobramycin, neomycin, kanamycin and netilmicin; a tetracycline such as chlortetracycline and doxycycline; chloramphenicol; a macrolide such as erythromycin; or miscellaneous antibiotics such as clindamycin, a polymyxin, and bacitracin for antibacterial, and in some cases antifungal infections; a polyene antibiotic such as amphotericin B, nystatin, and hamycin; flucytosine; an imidazole or a triazole such as ketoconazole, miconazole, itraconazole and fluconazole; griseofulvin for anti-Fungal diseases such as aspergillosis, candidaisis or histoplasmosis; zidovudine, acyclovir, ganciclovir, vidarabine, idoxuridine, trifluridine, an interferon (e.g, interferon alpha-2a or interferon alpha-2b) and ribavirin for anti-viral disease; aspirin, phenylbutazone, phenacetin, acetaminophen, ibuprofen, indomethacin, sulindac, piroxicam, diclofenac; gold and steroidal antiinflammatories for inflammatory diseases such as arthritis; an ACE inhibitor such as captopril, enalapril, and lisinopril; the organo nitrates such as amyl nitrite, nitroglycerin and isosorbide dinitrate; the calcium channel blockers such as diltiazem, nifedipine and verapamil; the beta adrenegic antagonists such as propranolol for cardiovascular disease; a diuretic such as a thiazide; e.g., benzothiadiazine or a loop diuretic such as furosemide; a sympatholytic agent such as methyldopa, clonidine, gunabenz, guanethidine and reserpine; a vasodilator such as hydralazine and minoxidil; a calcium channel blocker such as verapamil; an ACE inhibitor such as captopril for the treatment of hypertension; quinidine, procainamide, lidocaine, encainide, propranolol, esmolol, bretylium and diltiazem for the treatment of cardiac arrhythmia; lovostatin, lipitor, clofibrate, cholestryamine, probucol, and nicotinic acid for the treatment of hypolipoproteinemias; an anthracycline such as doxorubicin, daunorubicin and idambicin; a covalent DNA binding compound, a covalent DNA binding compound and a platinum compound such as cisplatin and carboplatin; a folate antagonist such as methotrexate and trimetrexate; an antimetabolite and a pyrimidine antagonist such as fluorouracil, 5-fluorouracil and fluorodeoxyuridine; an antimetabolite and a purine antagonist such as mercaptopurine, 6-mercaptopurine and thioguanine; an antimetabolite and a sugar modified analog such as cytarabine and fludarabine; an antimetabolite and a ribonucleotide reductase inhibitor such as hydoxyurea; a covalent DNA binding compound and a nitrogen mustard compound such as cyclophosphamide and ifosfamide; a covalent DNA binding compound and an alkane sulfonate such as busulfane; a nitrosourea such as carmustine; a covalent DNA binding compound and a methylating agent such as procarbazine; a covalent DNA binding compound and an aziridine such as mitomycin; a non covalent DNA binding compound; a non covalent DNA binding compound such as mitoxantrone and, bleomycin; an inhibitor of chromatin function and a topoisomerase inhibitor such as etoposide, teniposide, camptothecin and topotecan; an inhibitor of chromatin function and a microtubule inhibitor such as the vinca alkaloids including vincristine, vinblastin, vindisine, and paclitaxel, taxotere or another taxane; a compound affecting endocrine function such as prednisone, prednisolone, tamoxifen, leuprolide, ethinyl estradiol, an antibody such as herceptin; a gene such as the p-53gene, the p 16 gene, the MIT gene, and the gene E-cadherin; a cytokine such as the interleukins, particularly, IL-1, IL-2, IL-4, IL-6, IL-8 and IL-12, the tumor necrosis factors such as tumor necrosis factor-alpha and tumor necrosis factor-beta, the colony stimulating factors such as granulocyte colony stimulating factor (G-CSF), macrophage colony stimulating factor (M-CSF) and, granulocyte macrophage colony stimulating factor (GM-CSF) an interferon such as interferon-alpha, interferon -beta 1, interferon-beta 2, and interferon-gamma; all-trans retinoic acid or another retinoid for the treatment of cancer; an immunosuppressive agent such as: cyclosporine, an immune globulin, and sulfasazine, methoxsalen and thalidoimide; insulin and glucogon for diabetes; calcitonin and sodium alendronate for treatment of osteoporosis, hypercalcemia and Paget's Disease; morphine and related opioids; meperidine or a congener; methadone or a congener; an opioid antagonist such as nalorphine; a centrally active antitussive agent such as dexthromethrophan; tetrahydrocannabinol or marinol, lidocaine and bupivacaine for pain management; chlorpromazine, prochlorperazine; a cannabinoid such as tetrahydrocannabinol, a butyrophenone such as droperidol; a benzamide such as metoclopramide for the treatment of nausea and vomiting; heparin, coumarin, streptokinase, tissue plasminogen activator factor(t-PA) as anticoagulant, antithrombolytic or antiplatelet drugs; heparin, sulfasalazine, nicotine and steroids and tumor necrosis factor-alpha for the treatment of inflammatory bowel disease; nicotine for the treatment of smoking addiction; growth hormone, luetinizing hormone, corticotropin, and somatotropin for hormonal therapy; and adrenaline for general anaphylaxis.

The skilled person can easily determine experimentally if a certain compound incorporates well into the particles of the invention by the methods described in the examples below, e.g. example 9. For compounds that are not detectable by spectroscopic methods, the skilled person can rely e.g. on LC-MS or thin layer chromatography to determine if a certain compound incorporates well into the particles of the invention.

The benefit of including hydrophobic agents into the particles of the invention is that they effectively become solubilized in the stable structure of the particles, which thereby can serve as deposit and/or delivery vehicle for the hydrophobic agents in aqueous environment, which is e.g. present in the majority of body fluids and tissues. Compared to classic means of solubilization via detergents or organic solvents, the particles of the invention offer the advantage that from the outside they are hydrophilic whilst the hydrophobic agent is effectively solubilized in the hydrophobic interior of the particle, by which means the hydrophobic agent can maintain its native functionalities such as e.g. catalytic activity or ligand binding. Moreover, in contrast to most detergents and organic solvents, the particles of the invention seem to be biocompatible.

Besides hydrophobic organic compounds, the lipoprotein particles of the invention have also proven capable of stably incorporating hydrophobic biomolecules such as e.g. a protein comprising a hydrophobic moiety. According to the invention, proteins comprising a hydrophobic moiety can, for example, be selected from a membrane protein, an integral transmembrane protein, an integral monotopic membrane protein, a peripheral membrane protein, an amphitropic protein in a lipid-bound state, a lipid-anchored protein and a chimeric protein with a fused hydrophobic and/or transmembrane domain.

Integral membrane proteins are membrane proteins which are permanently bound to the lipid bilayer and usually require a detergent or apolar solvent to become displaced form the membrane. Transmembrane proteins are integral membrane proteins that span across the membrane at least once. Examples of transmembrane proteins that can be incorporated into the particles of the invention are G-protein coupled receptors (GPCRs), porters such as uniporters, symporter or antiporters, channels such as ion channels or enzymes.

Integral monotopic membrane proteins are permanently attached to the membrane only from one side and do not span across the membrane. This class includes membrane proteins that are tethered to the membrane via alpha-helical transmembrane anchors. Examples include cytochrome P450 oxidases and glycophorin A.

Peripheral membrane proteins are only temporarily or indirectly associated with the lipid bilayer or integral membrane proteins incorporated therein. Peripheral membrane proteins usually dissociate from membranes following treatment with a polar reagent with an elevated pH or high salt concentrations. Examples of peripheral membrane proteins include phospholipase A2 or C, lipoxygenases and cytochrome c.

Lipid-anchored proteins are bound to the lipid bilayer via lipidated, in particular prenylated or GPI-anchored amino acid residues. Examples include bacterial lipoproteins, G proteins and certain kinases.

Amphitropic proteins are proteins that exist in at least two conformational states, a lipid free, water-soluble state and a lipid bound state. Upon association with lipids, amphitropic proteins undergo a conformational change allowing them to become reversibly or irreversibly membrane-associated. Examples of amphitropic proteins are pore-forming toxins and antibacterial peptides.

The particles of the invention generally are considered disc-shaped, with a Stokes radius (hydrodynamic radius) $R_S$ in the range of from 2 nm to 200 nm, in particular from 3 nm to 150 nm, preferably from 3 nm to 100 nm. The skilled person knows how to determine the Stokes radius. This is preferably done by analytical gel filtration (size exclusion chromatography), in comparison with standards of known Stokes radii. In particular, the particles can be subjected to a gel filtration step on e.g. a Superdex 200 HR10 30 gel filtration column and eluted with a suitable buffer at pH 7.5 and 0.5 ml/min at room temperature. Absorbance is monitored at 280 nm for protein. The column is calibrated using a mixture of protein standards of known Stokes radii such as e.g. thyroglobulin 669 kDa ($R_S$=8.5 nm), ferritin 440 kDa ($R_S$=6.1 nm) catalase 232 kDa ($R_S$=4.6 nm), lactate dehydrogenase 140 kDa ($R_S$=4.1 nm), bovine serum albumin 66 kDa ($R_S$=3.55 nm) and horse heart cytochrome c 12.4 kDa ($R_S$=1.8 nm). The standard proteins should span $R_S$ values above and below that of the particle of interest. A calibration curve is generated by plotting the elution position vs $R_S$ for the standard proteins. This generally gives an approximately linear plot, but otherwise, it is satisfactory to draw lines between the points and read the $R_S$ of the protein of interest from its elution position on this standard curve.

In some embodiments, e.g. when a bulky hydrophobic agent or higher amounts of lipids are present in the particles, the Stokes radius will be larger than 3.2 nm, in particular at least 3.5 nm, at least 5.0 nm or at least 10.0 nm.

The particles of the invention, and in particular the substantially disc-like shape thereof, may also be examined via transmission electron microscopy or, if the particles are large enough via negative-stain electron microscopy and single particle analysis as described in Example 12 below.

Structural analysis has indicated that in the particles of the invention, the lipids assemble into a discoidal bilayer-like structure of discrete size in the interior of the particle. The lipid binding polypeptide component generally defines the boundary of the discoidal bilayer and provides structure and stability to the particle. In most embodiments, the interior of the particle includes a hydrophobic region (e. g., comprised of lipid fatty acyl chains). In contrast to liposomes, particles of the invention typically do not comprise a hydrophilic or aqueous core. The particles are generally disc-shaped, having a flat, discoidal, roughly circular lipid bilayer circumscribed by amphipathic α-helices provided by two or more lipid binding polypeptides, which are associated with hydrophobic surfaces of the bilayer around the periphery of the disc. Illustrative examples of disc-shaped particles of the invention are schematically depicted in FIGS. 2 to 7.

The discoidal shape of the particles of the invention can be approximated by a cylinder with a ratio of the maximum height to the maximum diameter (major axis length) of at least 1.0:1.1, in particular 1.0:1.5 or 1.0:2.0. The maximum height of the discoidal particle generally is at least 3.5 nm, in particular at least 5 nm, as determined by transmission electron microscopy or, if the particles are large enough, via negative-stain electron microscopy and single particle analysis. The particle of the invention has a top, a bottom and a circumferential side surface, with the maximum diameter (major axis length) of the top and bottom surface being larger than the height of the circumferential side surface. In some embodiments of the particle of the invention, the lipid binding polypeptide is at least partially located to surround the circumferential side surface of the particle.

In some embodiments of the invention, the maximum diameter (major axis length) of the disc-shaped particle of the invention, as determined by transmission electron microscopy or, if the particles are large enough, via negative-stain electron microscopy and single particle analysis is from between 2 nm to 200 nm, in particular from 3 nm to 150 nm, preferably from 3 nm to 100 nm. In another embodiment, the maximum diameter (major axis length) of the disc-shaped particle is from 3 nm to 80 nm, in particular from 3 nm to 60 nm. Practical experiments have shown that particles having a maximum diameter (major axis length) of 3 nm to 20 nm are particularly easily obtainable with the method of the invention.

In preferred embodiments of the invention, the particles are defined by a substantially monodisperse population of disk structures, as assessed by the gel filtration elution profile on for example a HiLoad Superdex™ 200 16/60 GL column.

Generally, the predominant interaction between the lipid binding polypeptide and a lipid bilayer in a particle is through hydrophobic interactions between residues on the hydrophobic faces of amphipathic α-helices of the lipid binding polypeptide molecules and hydrophobic surfaces of lipids, for example, phospholipid fatty acyl chains, at the edge of the bilayer at the periphery of the bioactive agent delivery particle. An amphipathic α-helix of lipid binding polypeptide molecule includes both a hydrophobic surface in contact with a hydrophobic surface of the lipid bilayer at the periphery of the particle, and a hydrophilic surface facing the exterior of the particle and in contact with the aqueous environment when the particle is suspended in aqueous medium.

In some embodiments, the particles are stable in aqueous solution and may be lyophilized for long term storage, followed by reconstitution in aqueous solution. "Stability" or "stable" as used herein means low to undetectable levels of particle fragmentation, low to undetectable levels of aggregation or quality deterioration during preparation, transportation, and storage of the particles.

In a preferred embodiment, the particles according to the invention are stable in aqueous solutions at a pH of from 5.0 to 8.0 and a temperature of from −210° C. to 4° C. for at least 1 day, at least 2 days, at least 7 days, at least 2 weeks, at least 1 month, at least 6 months or at least 12 months, as determined, for example, by visual inspection (clear and precipitate-free solution) or analytical gel filtration (less than 50%, in particular from 1 to 40% fragmentation of the particles). Practical experiments have shown that the particles of the invention are also stable at temperatures from 4° C. to 40° C. in aqueous solutions at a pH of from 5.0 to 8.0 for at least 1 day, at least 2 days, at least 7 days, at least 2 weeks, at least 1 month or at least 3 months as determined, for example, by visual inspection (clear and precipitate-free solution) or analytical gel filtration (less than 50%, in particular from 1 to 40% fragmentation of the particles). The particles of the invention have also proven to be stable in aqueous solutions at a pH of from 5.0 to 8.0 and a temperature of from 40° C. to 75° C. for at least 10 minutes, as determined, for example, by visual inspection (clear and precipitate-free solution) or analytical gel filtration (less than 50%, in particular from 1 and 40% fragmentation of the particles). In some embodiments, the particles may be lyophilized for long term storage, followed by reconstitution in aqueous solution. In some embodiments the particles of the invention are stable in lyophilized form at −210° C. to 40° C., in particular from −210° C. to 25° C. for at least 1 day, at least 2 days, at least 7 days, at least 2 weeks, at least 1 month, at least 6 months or at least 12 months, as determined, for example, by analytical gel filtration after reconstitution in an appropriate buffer at pH 7.5 (less than 50%, in particular less than 40% or from 1 to 40% fragmentation of the particles). "Fragmentation" as used herein means that in the gel filtration elution profile, the size of the peak (i.e. peak height) corresponding to the particle of the invention has decreased at the expense of the peak size of free non-lipid-bound SAPLIP and/or free lipids and/or aggregates, as compared to the peak size of the freshly prepared particle of the invention. Accordingly, a fragmentation of 40% for example means that the peak size (i.e. the height of the peak in the gel filtration elution profile) has decreased by 40% as compared to the peak size prior to storage (100%).

Practical experiments have shown that the particles of the invention are particularly stable also in aqueous solutions that are substantially free of detergents. Substantially free of detergents means that the aqueous solution comprises less than 0.001% (w/v) of detergent based on the total volume of the aqueous solution.

In a further aspect, the invention provides a process for the manufacture of a particle comprising a lipid binding polypeptide and lipids, wherein the lipid binding polypeptide is a SAPLIP or a derivative or truncated form thereof. The process comprises the steps of
(a) contacting the lipid binding polypeptide with solubilized lipids in a liquid environment; and
(b) allowing for the self-assembly of the particles at a pH of from 5.0 to 10 or 5.0 to 8.5; in particular from 6.0 to 8.0 and most preferably from 7.0 to 8.0.

In some embodiments of the process, the lipid binding polypeptide and the lipids are as described above.

In one embodiment of the process of the invention, the lipid binding polypeptide is contacted in step (a) with the solubilized lipids in an aqueous liquid. In certain embodiments, the aqueous liquid is a buffered solution at a pH of from 5.0 to 10.0 or from 5.0 to 8.5; in particular from 6.0 to 8.0 and most preferably from 7.0 to 8.0.

In a particular embodiment of the process of the invention, the lipids have been solubilized by means of an organic solvent or a detergent. Preferably, the lipids used in step (a) are in a detergent-solubilized state. Practical experiments have shown that a wide variety of detergents can be used to solubilize the lipids for being employed in the process of the invention. For example, the process of the invention works very well with lipids solubilized in solutions comprising 0.01 to 5.0%, in particular 0.1 to 1.0% alkyl glycosides such as short or longer chain alkyl maltosides and glucosides. However, depending on the type of lipids employed, other suitable detergents may be used as well. The ability of a given detergent to solubilize a given lipid or lipid mix can easily be inspected visually by the formation of a clear solution devoid of aggregates, precipitates or phase separation.

In contrast to the processes of the prior art, the lipids can be directly employed in the process of the invention without the need for an upstream liposome preparation step. This is advantageous as it simplifies the manufacturing process of the SAPLIP lipoprotein particles. In view of the solubilized nature of the lipids used as starting material for step (a) of the process of the invention, it is believed that the lipids are substantially not in the form of liposomes.

Practical experiments have shown that the lipid binding polypeptides of the invention generally do not require detergents or other solvents during purification, storage or handling. Optionally, however, also the lipid binding polypeptide used in step (a) can be in a detergent-solubilized state.

In one embodiment of the process of the invention, the molar ratio of lipid binding polypeptide to lipids in step (a) is at least 1:1, in particular at least 1:3, preferably at least 1:5 or 1:10.

In step (b) of the process of the invention, a pH of from 5.0 to 10.0, preferably of from 5.0 to 8.5, allows the components brought into contact with each other in step (a) to self-assemble into the particle of the invention. Contrary to the expectation based on the prior art that SAPLIP-lipoprotein particles should be best assembled at or close to the saposins' natural pH optimum of 4.75, it was found that SAPLIP-lipoprotein particles can be obtained by a simplified and reliable process if a more neutral or basic pH is maintained during preparation of the particles. Surprisingly, it was found that at a pH of from 5.0 to 10 and in the presence of solubilized lipids, purified saposin-like protein or a derivative or truncated form thereof self-assembles into stable lipoprotein particles without the need of an upstream liposome preparation step. This simple and reliable preparation method failed to yield satisfactory results when particle assembly was attempted at the saposins' natural pH optimum of 4.75 or in the absence of lipids.

Step (b) of the process of the invention may comprise diluting the mixture obtained in step (a) with a liquid that contains less amounts of detergent than the mixture obtained in step (a). Practical experiments have shown that such a dilution step further induces and facilitates the self-assembly of the particles of the invention. Without wanting to be bound by this theory, it is believed that such a dilution step effectively removes solvent or detergent molecules from the hydrophobic surfaces of the lipid binding polypeptide and the lipids, thereby triggering the particle self-assembly process of the invention via enhanced hydrophobic interactions of the components.

Whereas the particle self-assembly step (b) may take place in exactly the same composition as prepared in step (a), practical experiments have shown that preferably step (b) comprises an organic solvent/detergent removal or dilution step. Step (b) can, for example, be a gel filtration step. In certain embodiments, the mixture obtained in step (a) is subjected to a gel filtration step, whereby the gel filtration buffer or other solution is a liquid that contains less amounts of detergent than the mixture obtained in step (a).

In the process of the invention step (a) and/or (b) is preferably performed at a temperature of from 1° C. to 95° C., in particular from 15° C. to 80° C., particularly preferred at 30° C. to 40° C., and/or near the gel to liquid crystalline phase transition temperature of the lipids used. The phase transition temperature of the lipids used can easily be found in the literature or determined by calorimetry.

According to one embodiment of the process of the invention in step (b) or in an optional subsequent step (c) a purification of the particles of the invention by at least partial removal of free lipids and/or free lipid binding polypeptide is performed. Suitable purification methods are chromatographic methods, in particular size-exclusion chromatography, ultracentrifugation, dialysis, contacting with detergent-binding biobeads, use of concentrators, affinity chromatography, magnetic beads and/or membrane/filters to remove unbound/non-incorporated lipids and/or hydrophobic compounds.

The products of the process of the invention are particles comprising the lipid binding polypeptide and the lipid component. These particles of the invention are referred to as Salipro particles in the further description of the invention and in certain embodiments can have any or all of the characteristics described above for the Salipro particles comprising a lipid binding polypeptide, lipids and a hydrophobic agent.

The process of the invention can also be used to incorporate a hydrophobic agent into Salipro particles, thereby resulting in product particles comprising a lipid binding polypeptide, lipids and a hydrophobic agent. The hydrophobic agent can have any or all of the characteristics described above for the various hydrophobic agents that can be comprised in the particles of the invention.

If Salipro particles with an incorporated hydrophobic agent shall be prepared, step a) of the process of the invention is simply modified in that the lipid binding polypeptide is contacted with lipids in a liquid environment comprising the hydrophobic agent that is to be incorporated into the particle. Practical experiments have shown that the process of the invention allows for stable incorporation of both hydrophobic organic compounds, such as for example curcumin, as well as monomeric or oligomeric membrane proteins into the particles of the invention.

According to a particular embodiment, step (a) and/or (b) are preferably performed at a temperature of from 20° C. to 80° C., in particular from 20° C. to 70° C., particularly preferred at 30° C. to 70° C. Whereas a temperature of between 30° C. to 40° C. in step (a) and/or (b) is sufficient for most compounds, practical experiments have shown that for certain hydrophobic agents, the load of hydrophobic agent incorporated into the particles of the invention can be increased by raising the temperature in step (a) and/or (b) to higher temperatures, such as in the range of from 50° C. to 70° C. By the methods taught herein, the skilled person can determine the optimal incubation temperature with regards to the temperature stability of the compounds, lipids and proteins used and the load of hydrophobic agent desired for the intended application.

In one embodiment, the hydrophobic agent has been solubilized by means of a suited organic solvent (such as for example DMSO, methanol and/or chloroform) or a detergent prior to being employed in step (a). Preferably, the hydrophobic agent used in step (a) is in a detergent-solubilized state. The detergent can be the same or different from the detergent used to solubilize the lipids.

In one embodiment of the invention, the detergent used to solubilize the lipids and/or the hydrophobic agent that are/is employed in step (a) is not carried over in substantial amounts into the finished particles of the invention. In particular, the amount of detergent in the particles obtainable by the process of the invention can be low to undetectable. In one embodiment, the particle of the invention does not comprise any substantial amounts of detergent, in particular less than 0.1 wt-%, preferably less than 0.01 wt-%, particularly preferred less than 0.001 wt-% detergent based on the weight of the particle. The amount of detergent present in the particles can be determined, for example, by mass spectrometry.

If the hydrophobic agent used in step (a) is in a detergent-solubilized state, practical experiments have shown that it is advantageous to use detergents for purification and/or solubilization of the hydrophobic agent with short- to medium-chain hydrophobic tails. This is particularly true if a membrane protein is incorporated as hydrophobic agent. "Short chain hydrophobic tails" as used herein means C2 to C9, such as for example in n-Nonyl-β-maltoside (NM); "medium chain hydrophobic tails" as used herein means C10 to C15, such as for example in n-Decyl-β-maltoside (DM) or n-Dodecyl-β-maltoside (DDM). In one embodiment, the detergent used for purification and/or solubilization of the hydrophobic agent has from 2 to 12 carbon atoms in its hydrophobic tail, preferable from 2 to 10 and most preferred from 2 to 9 carbon atoms in its hydrophobic tail.

In some embodiments, the molar ratio of lipid binding polypeptide to hydrophobic agent in step (a) is at least 1:0.5, preferably at least 1:2 or at least 1:5, particularly preferred at least 1:10. In another embodiment, the molar ratio of lipid binding polypeptide to hydrophobic agent in step (a) is from 1:0.5 and 1:10000, in particular from 1:0.5 and 1:1000 or from 1:0.5 and 1:500. Practical experiments have shown that the stoichiometry of components in and the size of the resulting particles can be controlled by adjusting the ratio of the starting components accordingly.

For most hydrophobic agents to be incorporated into the particles of the invention, optimal results are achieved if the molar ratio of lipids to hydrophobic agent in step (a) is from 10000:1 to 1:1000, in particular from 10:1 to 0.5:1.

The invention is also directed to the particle obtainable by the process of the invention described above, i.e. irrespective of the process that was actually used to prepare the particle.

The particles obtainable by the process of the invention differ from the particles of the prior art in multiple features, for example by their inherent size flexibility and ability to adapt to the respective size of the hydrophobic agent that is to be incorporated into the lipoprotein particles.

The invention also provides a pharmaceutical composition for delivering a hydrophobic agent to an individual in need thereof, wherein the composition comprises particles of the invention and wherein the hydrophobic agent is an active ingredient and/or wherein in addition to the hydrophobic agent an active ingredient is present.

Besides the particles of the invention, the pharmaceutical composition can optionally comprise a (further) pharmaceutically acceptable vehicle, carrier or adjuvant.

When the particles of the invention are for use in a pharmaceutical composition, the individual components of the particles and the pharmaceutical composition should be pharmaceutically acceptable. As used herein, the term "pharmaceutically acceptable" refers to components, compounds or agents that are, within the scope of sound medical judgment, suitable for use in contact with the tissues of humans and lower animals without undue toxicity, irritation, allergic response and the like, and are commensurate with a reasonable benefit/risk ratio.

In yet another aspect, the invention provides a method of treating an individual in need thereof, with a therapeutically effective amount of the pharmaceutical composition described above. A "therapeutically effective amount" of the pharmaceutical composition, as used herein, is that amount effective for treating or lessening the severity of the disease or condition to be treated. The term "individual", as used herein, means an animal, for example, a mammal, and more specifically a human.

The pharmaceutical compositions of this invention can be administered to humans and other animals orally, rectally, parenterally, intracisternally, intravaginally, intraperitoneally, topically (as by powders, ointments, or drops), bucally, as an aerosol, an oral or nasal spray, or the like, depending on the severity of the disease or condition being treated. In particular, the pharmaceutical composition can be formulated for enteral, parenteral and/or topical administration. It can be administered as a capsule, infusion or injection, a brushable or potable composition or as an aerosol. In some embodiments of the pharmaceutical composition of the invention, the particles of the invention are present in solid form, as a dispersion or in solution.

The particles of the invention are also useful for diagnostic and/or cosmetic applications. For example, particles which comprise detectable substances, such as labels, markers or indicators, may be used as diagnostic agents and applied for diagnostic purposes. The labels, markers or indicators may themselves be comprised in or formed by the hydrophobic agent, however they may also be attached to the lipid binding polypeptide or the lipid components of the particle. Examples of diagnostic and life science research tools according to the invention include particles with labeled incorporated hydrophobic proteins, labeled lipid binding polypeptide, labeled lipids, incorporated fluorophores or contrast agents (for example for MR imaging). The label can for example be a fluorescent label.

Further, the particles of the invention are useful as a tool for drug development, drug screening and/or membrane protein research.

For example, a membrane protein drug target, such as a cell surface receptor or ion channel, may be incorporated into the particles of the invention and solubilized thereby. Such particles can then be employed in assays to study the activity of the drug target membrane protein in its native lipid bilayer environment or used in drug screenings to identify new drugs.

Moreover, the particles of the invention may also be fixed to a solid support making them useful for applications such as Surface Plasmon Resonance (SPR) or biosensor applications.

The particles of the invention are generally useful for rendering otherwise insoluble membrane proteins soluble in aqueous solutions in a native-like bilayer microenvironment. Hence, the invention provides a wide variety of new applications in membrane protein research. For example, the particles of the invention allow studying membrane proteins incorporated in the particles of the invention by methods such as nuclear magnetic resonance (NMR), X-ray crystallography, electron microscopy (EM), mass spectrometry, isothermal titration calorimetry (ITC), differential light scattering, small-angle X-ray scattering (SAXS) and the like. In another aspect, the particles of the invention are useful as vaccination formulation, as carrier thereof or as drug delivery vehicle. Many pathogenic antigens that could be particularly potent in vaccinations are exposed on the surface and/or comprised in the outer cell membrane of the pathogens, i.e. derived from pathogenic lipids, other hydrophobic biomolecules or membrane proteins. For example, the major antigens on Influenza viruses are present in the integral membrane protein Hemagglutinin. With the particles of the invention, such pathogenic hydrophobic biomolecules can effectively be incorporated into the particles which then can be used as antigen-presenting delivery vehicles in vaccination formulations. Along these lines, the particles of the invention are also useful to serve as antigen-presenting delivery vehicles for generating antibodies against hydrophobic agents or biomolecules in suitable host animals such as e.g. rabbits, goats or lamas.

Furthermore, the particle of the invention can be used in cosmetics, in particular wherein the particle of the invention includes skin nourishing and/or nurturing agents, such as vitamins and/or antioxidants.

BRIEF DESCRIPTION OF THE DRAWINGS

Further features and advantages of the invention will emerge from the following detailed description of some of its embodiments shown by way of non-limiting examples in the accompanying drawings, in which:

FIG. 1 is a schematic illustration of the shape and molecular organization of the Apolipoprotein A-1 containing nanosdisc particles of the prior art (e.g. EP 1 596 828 B1 discussed above).

FIG. 2 is a schematic illustration of Salipro particles according to the invention comprising hydrophobic organic compounds and their preparation; depicted in a) as side view and in b) as top view.

FIG. 3 is a schematic illustration of Salipro particles according to the invention comprising a membrane protein and their preparation; depicted in a) as side view and in b) as top view.

FIG. 4 is a schematic illustration of Salipro particles according to the invention comprising a membrane protein and hydrophobic organic compounds and their preparation; depicted in a) as side view and in b) as top view.

FIG. 7 is a schematic illustration of Salipro particles according to the invention and their preparation; depicted in a) as side view and in b) as top view.

FIG. 8 is a gel filtration elution profile of Salipro particles ("Saposin+Lipids pH 7.5") according to the invention and comparison experiments ("Saposin+Lipids pH 4.75"; "Saposin pH 7.5") as described in Example 2.

FIG. 9 is a gel filtration elution profile of Salipro particles ("Saposin+LDAO+Lipids pH 7.5") according to the invention and comparison experiments ("Saposin+LDAO pH 7.5"; "Saposin+LDAO pH 4.75"; "Saposin+LDAO+Lipids pH 4.75") as described in Example 3.

FIG. 10 is a gel filtration elution profile of Salipro particles according to the invention using a variety of different lipids as described in Example 4.

FIG. 11 is a gel filtration elution profile of Salipro particles comprising the membrane protein YbgH ("Saposin+Detergent+Lipids+MemProt YbgH pH 7.5") according to the invention and comparison experiments ("Saposin+Detergent+Lipids+MemProt YbgH pH 4.75"; "Saposin+Detergent+MemProt YbgH pH 7.5"; "Saposin+Detergent+MemProt YbgH pH 4.75") as described in Example 5.

FIG. 12 is a gel filtration elution profile of Salipro particles ("Saposin+Detergent+Lipids") and Salipro particles comprising the membrane protein MATE ("Saposin+Detergent+Lipids+MemProt MATE") according to the invention and comparison experiments ("Saposin"; "Saposin+Detergent+MemProt MATE") as described in Example 6.

FIG. 19 is a gel filtration elution profile of Salipro particles according to the invention that were subjected to different heat treatments as described in Example 13.

FIG. 1 depicts—in schematic form—the shape and molecular organization of the Apolipoprotein A-1 containing nanosdisc particles 10 of the prior art (e.g. EP 1 596 828 B1 discussed above). The particle of the prior art 10 is disc-shaped comprising an apolipoprotein scaffold protein 11 which tightly surrounds a lipid bilayer formed by lipids 3 in a double belt-like fashion. The interior of said particles is formed by the hydrophobic region of the lipids 3 in the lipid bilayer. The Stokes diameter of the particle 10 is in the range of 10 nm.

FIG. 2 depicts—in schematic form—the preparation as well as shape and molecular organization of Salipro particles 1 according to the invention comprising hydrophobic organic compounds 4, depicted in a) as side view and in b) as top view.

Figure 5B:
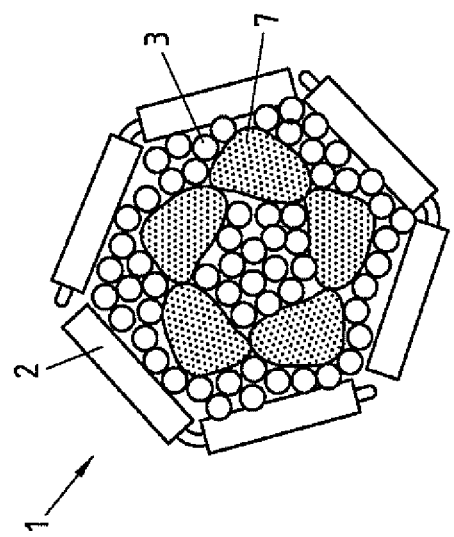
FIG. 5 is a schematic illustration of Salipro particles according to the invention comprising an oligomeric membrane protein; depicted in a) as side view and in b) as top view.

The particle 1 of the invention is prepared by mixing purified lipid binding polypeptide 2 with lipids 3 and the hydrophobic organic compounds 4 to be incorporated and allowing the self-assembly of the particle 1 at a pH of from about 5.0 to about 10.0. The lipid binding polypeptide 2 is a saposin-like protein (SAPLIP) and comprises 4 amphipathic helices which are depicted as cylinders. The lipids 3 are amphiphilic comprising a hydrophilic head group (depicted as circle) and hydrophobic tails such as fatty acyl chains (depicted as zigzag line). As is the case also for the following FIGS. 3 to 6, a detailed description of the general structural features of particle 1 and its lipid 3 and SAPLIP 2 components can be found in the description of the basic lipid-only Salipro particle of the invention below which is depicted in FIG. 7.

In the particle 1, the hydrophobic organic compounds 4 are embedded in the hydrophobic portion of the lipid bilayer formed by the lipids 3. The hydrophobic organic compound 4 can, for example, be a biologically active agent, a drug, an active ingredient of a drug, an active ingredient of a cosmetic product, an active ingredient of a plant protective product, a dietary and/or nutritional supplement, a diagnostic probe, a contrast agent, a label and/or an indicator.

Figure 5A:
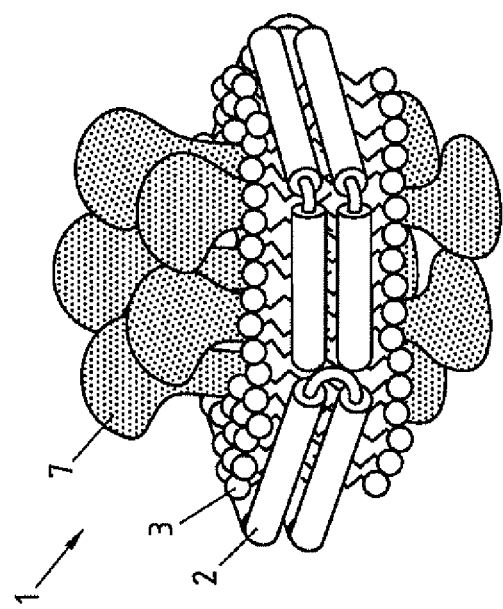

FIG. 3 depicts—in schematic form—the preparation as well as shape and molecular organization of Salipro particles 1 comprising an integral monomeric membrane protein 5 according to the invention, depicted in a) as side view and in b) as top view. The membrane protein 5 can be an integral transmembrane protein in monomeric form, as depicted in FIGS. 3 and 4. However, it can also be in an oligomeric state as depicted in FIG. 5 or a peripheral membrane protein, an amphitropic protein in a lipid-bound state, a lipid-anchored protein or a chimeric protein with a fused hydrophobic and/or transmembrane domain, all of which may be in a monomeric or oligomeric state.

The particle 1 of the invention is prepared by mixing purified SAPLIP 2 with lipids 3 and the membrane protein 5 to be incorporated and allowing the self-assembly of the particle 1 at a pH of from about 5.0 to about 10.0. The membrane protein 5 can be associated with detergent molecules 6 and/or lipids 12. The detergent molecules 6 can come from the purification and/or solubilization of the membrane protein 5. The lipids 12 associated with the membrane protein 5 can be a carry-over from the membrane protein's native lipid environment prior to its purification. In the particle 1, the membrane protein 5 is embedded in the hydrophobic portion of the lipid bilayer and adopts a similar conformation as in its native membrane-bound state. The particle 1 may optionally comprise lipids 12 and/or detergent molecules 6 derived from the purified membrane protein 5. In certain embodiments, the particle 1 does not comprise any substantial amounts of detergent molecules 6, in particular less than 0.1 wt-% detergent molecules based on the weight of the particle.

The particle of the invention 1 is flexible in size. Schematic FIGS. 2 to 7 are not drawn to scale. Depending on the size of the membrane protein 5 incorporated in the particle 1, the particle depicted in FIG. 3 can be substantially larger than the lipid-only particle depicted in FIG. 7 or the particle comprising low molecular weight organic hydrophobic compounds 4 as depicted in FIG. 2. Generally, an increase in particle size will also be reflected by the number of SAPLIP molecules 2 per particle, which can be more than two. The particle of the invention may for example comprise two to twenty, in particular two to ten SAPLIP molecules 2. The size of the particle 1 can also be influenced by the amounts of lipids 3 added in step (a) of its preparation.

FIG. 4 depicts—in schematic form—the preparation as well as shape and molecular organization of Salipro particles 1 comprising an integral monomeric membrane protein 5 and hydrophobic organic compounds 4 according to the invention, depicted in a) as side view and in b) as top view. The particle 1 of the invention is prepared by mixing purified SAPLIP 2 with lipids 3, the membrane protein 5 and the hydrophobic organic compounds 4 to be incorporated and allowing the self-assembly of the particle 1 at a pH of from about 5.0 to about 10.0.

FIG. 5 is a schematic illustration of Salipro particles 1 according to the invention comprising an oligomeric membrane protein 7; depicted in a) as side view and in b) as top view. The particle 1 is flexible in size and adapts to the size of the hydrophobic agent 7 incorporated therein. In the embodiment depicted in FIG. 5, the particle 1 comprises three SAPLIP molecules 2 per particle which are arranged in a head-to-tail fashion. The hydrodynamic radius of a particle comprising three SAPLIP molecules is in the range of from 5 to 20 nm, depending on the hydrophobic agent incorporated therein.

Figure 6:
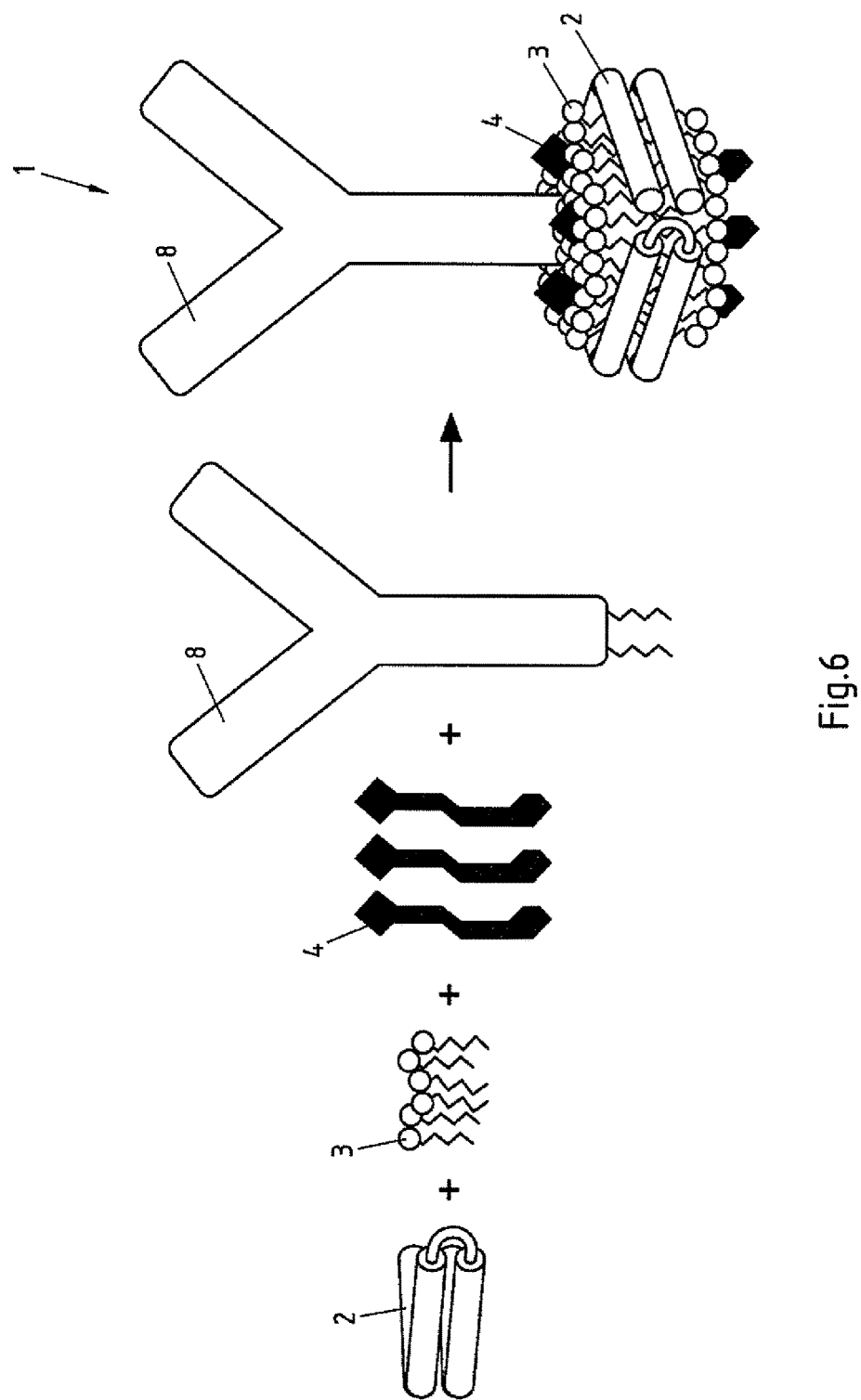
FIG. 6 is a schematic illustration of Salipro particles according to the invention comprising a targeting component such as an antibody and hydrophobic organic compounds and their preparation.

FIG. 6 depicts—in schematic form—the preparation as well as shape and molecular organization of Salipro particles 1 comprising a targeting component such as an antibody 8 and hydrophobic organic compounds 4. The targeting component 8 may be in the form of a lipid-anchored protein as depicted in FIG. 6 or in the form of a chimeric protein with a fused hydrophobic and/or transmembrane domain. The targeting component may also be attached to or comprised in either the lipid binding polypeptide 2, one of the lipids 3 and/or the hydrophobic compound 4.

FIG. 7 depicts—in schematic form—the preparation as well as shape and molecular organization of Salipro particles according to the invention. The particle 1 of the invention is prepared by mixing purified SAPLIP 2 with lipids 3 and allowing the self-assembly of the particle 1 at a pH of from about 5.0 to about 10.0. The lipids 3 are amphiphilic comprising a hydrophilic head group (depicted as circle) and hydrophobic tails such as fatty acyl chains (depicted as zigzag line). In the "closed" apo state (cf. FIG. 7a, left side) the conformation of the SAPLIP 2 is different as compared to its lipid-bound "open" conformation in the particle of the invention 1 (cf. FIG. 7a, right side). In the closed state, the SAPLIP 2 adopts a four-helix-bundle-type structure with the hydrophobic portions of its amphipathic helices facing the inside of the four-helix bundle. In the "open" lipid-bound conformation in particle 1, the SAPLIPs 2 adopt a V-shaped or boomerang-shaped conformation (cf. FIG. 7b and FIG. 7a, right side) with the hydrophobic portions of its amphipathic helices contacting the hydrophobic region of the lipids 3 in the lipid bilayer.

FIG. 7a shows the particle 1 and its preparation as side view, FIG. 7b as top view. The particle of the invention 1 is approximately disc-shaped, having a flat, discoidal, roughly circular to square-shaped lipid bilayer circumscribed by the amphipathic α-helices of two SAPLIP molecules 2. The lipids 3 assemble into a discoidal bilayer-like structure of discrete size in the interior of the particle 1. The SAPLIPs 2 define the boundary of the discoidal bilayer in the particle 1, the interior of which is hydrophobic, i.e. comprised of lipid fatty acyl chains and lacking a hydrophilic or aqueous core. The particle 1 is held together mainly by the hydrophobic interactions of the lipids 3 within the bilayer core of the particle 1 and hydrophobic interactions between the lipids 3 and the hydrophobic portions of the amphiphilic helices of the SAPLIPs 2 facing the interior of the particle. The SAPLIPs 2 are arranged in a head-to-tail fashion and there are substantially no intermolecular protein-protein contacts between the SAPLIPs 2 in the particle 1. In its smallest form, the particle 1 is thought to contain two SAPLIP molecules 2 and at least around 10 lipid molecules 3. However, the particle of the invention 1 is flexible in size. Depending on its size and the molar ratio of components used in its preparation, it can accommodate multiple, i.e. more than two, SAPLIP molecules 2, many more lipids 3 and optionally further components. For example, the particle may contain two to twenty, in particular two to ten SAPLIP molecules 2.

The maximum height of the Salipro particle 1 in its lipid-only form corresponds to the height of the lipid bilayer and is about 5 nm. The particle 1 has a top (seen in FIG. 7b), a bottom and a circumferential side surface, with the maximum diameter (major axis length) of the top and bottom surface being larger than the height of the circumferential side surface.

EXAMPLES

The following examples serve to further explain the invention in more detail, specifically with reference to certain embodiments and figures, which, however, are not intended to limit the present disclosure.

I

Abbreviations

The following abbreviations will be used:
POT1: Prokaryotic Membrane Protein, Peptide Transporter
POT2: Prokaryotic Membrane Protein, Peptide Transporter
MATE: Prokaryotic Membrane Protein, MATE Transporter
SYP: Human Membrane Protein
YbGH Prokaryotic Membrane Protein (from *Escherichia coli*), Peptide Transporter (also known as DtpD)
DDM: Dodecyl-β-D-Maltoside
LDAO: N,N-dimethyldodecylamine-N-oxide;
PS: phosphatidylserine
POPC: 2-oleoyl-1-pamlitoyl-sn-glycero-3-phosphocholine
POPG: 2-oleoyl-1-pamlitoyl-sn-glycero-3-glycerol
TEV: Tobacco Etch Virus
TCEP: tris(2-carboxyethyl)phosphine
RT: room temperature
Saposin A: 1.2 mg/ml saposin A (human), 20 mM Hepes pH 7.5, 150 mM NaCl
Brain-lipid-solution: 5 mg/ml brain lipids, 50 mM Hepes pH 7.5, 150 mM NaCl, 0.28% (w/v) DDM
Brain lipids: Sigma-Aldrich, Brain Extract from bovine brain, Type I, Folch Fraction I; B-1502
GF-buffer pH 7.5: 50 mM Hepes pH 7.5, 150 mM NaCl)
GF-buffer pH 4.75: 50 mM sodium acetate pH 4.75, 150 mM NaCl

II

Purification of Saposin a

Example 1

Purified saposin A was prepared as follows. Saposin A protein expression was carried out using a vector with the coding region for human saposin A (SEQ ID NO: 1) inserted into a pNIC-Bsa4 plasmid and transformed and expressed in *E. coli* Rosetta gami-2 (DE3) (Novagen) strains. Cells were grown at 37° C. in TB medium supplemented with Tetracycline, Chloramphenicol and Kanamycin and induced with 0.7 mM IPTG. Three hours after induction, the cells were collected by centrifugation at 12.000×g for 15 min. The supernatant was discarded, the cell pellet was resuspended using lysis buffer (20 mM Hepes pH 7.5, 150 mM NaCl, 20 mM Imidazol) and disrupted by sonication. Lysates were subjected to centrifugation at 26.000×g for 30 min, the supernatant heated to 85° C. for 10 min, followed by an additional centrifugation step at 26.000×g for 30 min. Preparative IMAC purification was performed by batch-adsorption of the supernatant by end-over-end rotation with Ni Sepharose™ 6 Fast Flow medium for 60 min. After binding of saposin A to the IMAC resin, the chromatography medium was packed in a 10-mm-(i.d.) open gravity flow column and unbound proteins were removed by washing with 15 bed volumes of lysis buffer. The resin was washed with 15 bed volumes of wash buffer WB2 (20 mM Hepes pH 7.5, 150 mM NaCl, 40 mM Imidazol). Saposin A was eluted by addition of five bed volumes of elution buffer EB (20 mM Hepes pH 7.5, 150 mM NaCl, 400 mM Imidazol). The eluate was dialyzed overnight against gel filtration buffer GF pH 7.5 (20 mM Hepes pH 7.5, 150 mM NaCl) supplemented with recombinant TEV protease. TEV protease containing an un-cleavable His-tag was removed from the eluate by passing it over 2 ml IMAC resin. Cleaved target proteins were concentrated to a volume of 5 ml using centrifugal filter units and loaded onto a HiLoad Superdex™ 200 16/60 GL column using an ÄKTAexplorer™ 10 chromatography system (both GE Healthcare). Peak fractions were pooled and concentrated to 1.2 mg/ml protein. The protein sample was flash frozen in liquid nitrogen and stored at −80 C.

III

Generation of Salipro Particles

Example 2

For the reconstitution of Salipro particles (denoted "Saposin+Lipids pH 7.5" in FIG. 8), 10 μl of purified saposin A (1.2 mg/ml, 20 mM Hepes pH 7.5, 150 mM NaCl) were mixed with 1.6 μl of a 1% (w/v) LDAO-detergent solution and 4 μl of a brain-lipid solution (5 mg/ml brain lipids, Sigma-Aldrich; 50 mM Hepes pH 7.5, 150 mM NaCl, 0.28% (w/v) DDM) and incubated for 10 min at 37° C. Subsequently, 49.4 μl GF-buffer pH 7.5 was added to the mixture to obtain a final reaction volume of 65 μl. After 10 min incubation at room temperature, the mixture was subjected to a gel-filtration step on a Superdex™ 200 5/150 GL analytical gel filtration column using an ÄKTAmicro™ chromatography system (both GE Healthcare) equipped with the Autosampler A-905, which automatically injected 25 µl of protein containing sample. Analytical gel filtration runs were performed at 4° C. at a flow rate of 0.2 ml/min in GF-buffer pH 7.5.

Comparative Example 2

Example 2 was performed again, with the exception that, instead of GF-buffer pH 7.5, GF-buffer pH 4.75 was used (denoted "Saposin+Lipids pH 4.75" in FIG. 8).

As negative control (denoted "Saposin pH 7.5" in FIG. 8), 10 µl of purified saposin A were incubated for 10 min at 37° C. Subsequently, 55 µl GF-buffer pH 7.5 was added to the mixture to obtain a final reaction volume of 65 µl. After 10 min incubation at room temperature, the mixture was subjected to a gel-filtration step, as described above.

Incubation of saposin A with brain lipids at pH 7.5 as in Example 2 resulted in a shift of the peak towards higher molecular weight stable lipid-protein particles (cf. "Saposin+Lipids pH 7.5" in FIG. 8). In contrast, no stable lipid-protein particles were observed after incubation with brain lipids at pH 4.75 as in Comparative Example 2 (cf. "Saposin+Lipids pH 4.75" in FIG. 8).

Example 3

The aim of this experiment was to assess the importance of the presence of lipids for the method according to the invention.

10 µl of purified saposin A (1.2 mg/ml, 20 mM Hepes pH 7.5, 150 mM NaCl) were mixed with 1.6 µl of a 1% (w/v) LDAO-detergent solution and 4 µl of a brain-lipid solution (5 mg/ml brain lipids, Sigma-Aldrich; 50 mM Hepes pH 7.5, 150 mM NaCl, 0.28% (w/v) DDM) and incubated for 10 min at 37° C. Subsequently, 49.4 µl GF-buffer pH 7.5 was added to the mixture to obtain a final reaction volume of 65 µl. After 10 min incubation at room temperature, the mixture was subjected to a gel-filtration step as above, using GF-buffer 7.5 (cf. "Saposin+LDAO+Lipids pH 7.5" in FIG. 9).

Comparative Example 3

10 µl of purified saposin A were mixed with 1.6 µl LDAO-detergent (1%) and 4 µl of a brain-lipid solution and incubated for 10 min at 37° C. Subsequently, 49.4 µl GF-buffer pH 4.75 was added to the mixture to obtain a final reaction volume of 65 µl. After 10 min incubation at room temperature, the mixture was subjected to a gel-filtration step as above, using GF-buffer 4.75 (cf. "Saposin+LDAO+Lipids pH 4.75" in FIG. 9).

In an attempt to generate stable saposin A-detergent particles with the method of the invention (denoted "Saposin+LDAO pH 7.5" in FIG. 9), 15 µl of purified saposin A (1.2 mg/ml, 20 mM Hepes pH 7.5, 150 mM NaCl) were mixed with 1.6 µl of a 1% (w/v) LDAO-detergent solution and incubated for 10 min at 37° C. Subsequently, 48.4 µl GF-buffer pH 7.5 was added to the mixture to obtain a final reaction volume of 65 µl. After 10 min incubation at room temperature, the mixture was subjected to a gel-filtration step on a Superdex™ 200 5/150 GL analytical gel filtration column using a ÄKTAmicro™ chromatography system (both GE Healthcare) equipped with the Autosampler A-905, which automatically injected 25 µl of protein containing sample. Analytical gel filtration runs were performed at 4° C. at a flow rate of 0.2 ml/min in GF-buffer pH 7.5.

The experiment was performed again as described in the previous paragraph with the exception that, instead of GF-buffer pH 7.5, GF-buffer pH 4.75 was used (cf. "Saposin+LDAO pH 4.75" in FIG. 9).

The results, which are depicted in FIG. 9, demonstrate that the process for preparing Salipro particles according to the invention requires the presence of lipids (cf. Example 3 and "Saposin+LDAO+Lipids pH 7.5" in FIG. 9 and Comparative Example 3 and "Saposin+LDAO pH 7.5" in FIG. 9) and fails to yield stable particles at a lysosomal pH of 4.75 as in Comparative Example 3 (cf. "Saposin+LDAO+Lipids pH 7.5" and "Saposin+LDAO+Lipids pH 4.75" in FIG. 9). Whereas the presence of detergent did not hinder the formation of stable Salipro particles, it was not possible to obtain the particles of the invention in the presence of detergent alone (cf. Example 3 and "Saposin+LDAO+Lipids pH 7.5" in FIG. 9 and Comparative Example 3 and "Saposin+LDAO pH 7.5" in FIG. 9).

Example 4

POPG, POPC, brain lipids and PS (from Sigma-Aldrich or Avanti Polar Lipids, all in powder form) were dissolved to 20 mg/ml in GF-buffer pH 7.5 supplemented with 1% (w/v) DDM, incubated for 1 h at 37° C. with intermediate vortex-mixing and stored at −80° C. For use, the lipid solutions were diluted to 5 mg/ml with GF-buffer pH 7.5 supplemented with 0.03% (w/v) DDM, leading to a final composition of 5 mg/ml lipids, 50 mM Hepes pH 7.5, 150 mM NaCl, 0.28% (w/v) DDM.

10 µl of purified saposin A (1.2 mg/ml, 20 mM Hepes pH 7.5, 150 mM NaCl) were mixed with 5 µl of the respective lipid solution (PG, PC, brain lipids, PS) and incubated for 10 min at 37° C. Subsequently, 45 µl GF-buffer pH 7.5 supplemented with 0.03% (w/v) DDM were added to the mixture to obtain a final reaction volume of 65 µl. After 10 min incubation at room temperature, the mixture was subjected to a gel-filtration step on a Superdex™ 200 5/150 GL analytical gel filtration column using an ÄKTAmicro™ chromatography system (both GE Healthcare) equipped with the Autosampler A-905, which automatically injected 25 µl of protein containing sample. Analytical gel filtration runs were performed at 4° C. at a flow rate of 0.2 ml/min in GF-buffer pH 7.5 (cf. "Saposin+PG", "Saposin+PC", "Saposin+brain lipids" and "Saposin+PS" in FIG. 10).

As a negative control, 10 µl of purified saposin A were incubated for 10 min at 37° C. Subsequently, 55 µl GF-buffer pH 7.5 was added to the mixture to obtain a final reaction volume of 65 µl. After 10 min incubation at room temperature, the mixture was subjected to a gel-filtration step, as above (cf. "Saposin" in FIG. 10).

The results, which are depicted in FIG. 10, demonstrate that the process for preparing Salipro particles according to the invention works with a variety of different lipids. Of note, the size of the Salipro particles is variable and can be influenced, for example, by the lipids used in the preparation of the particles (cf. FIG. 10).

IV

Salipro Particles Comprising Proteinaceous Hydrophobic Agents

To demonstrate the capability of Salipro particles as carriers for hydrophobic biomolecules, membrane proteins were incorporated into the Salipro nanoparticles of the invention by using the same approach described above, i.e.

mixing purified saposin A with lipids and the membrane protein to be incorporated at physiological pH followed by gel filtration.

Example 5

For the reconstitution of Salipro particles comprising the bacterial membrane protein YbgH (Salipro-YbgH, denoted "Saposin+Detergent+Lipids+MemProt YbgH pH 7.5" in FIG. 11), 10 µl of purified saposin A (1.2 mg/ml, 20 mM Hepes pH 7.5, 150 mM NaCl) were mixed with 1.6 µl of a 1% (w/v) LDAO-detergent solution and 4 µl of a brain-lipid solution (5 mg/ml brain lipids, Sigma-Aldrich; 50 mM Hepes pH 7.5, 150 mM NaCl, 0.28% (w/v) DDM) and 2.6 µl of purified membrane protein YbgH (10 mg/ml, 20 mM Hepes pH 7.5, 150 mM NaCl, 5% glycerol, 0.03% (w/v) DDM, 0.5 mM TCEP) and incubated for 10 min at 37° C. Subsequently, 46.8 µl GF-buffer pH 7.5 were added to the mixture to obtain a final reaction volume of 65 µl. After 10 min incubation at room temperature, the mixture was subjected to a gel-filtration step on a Superdex™ 200 5/150 GL analytical gel filtration column using a ÄKTAmicro™ chromatography system (both GE Healthcare) equipped with the Autosampler A-905, which automatically injected 25 µl of protein containing sample. Analytical gel filtration runs were performed at 4° C. at a flow rate of 0.2 ml/min in GF-buffer 7.5.

Comparative Example 5

Example 5 was performed again as described, with the exception that, instead of GF-buffer pH 7.5, GF-buffer pH 4.75 was used (cf. "Saposin+Detergent+Lipids+MemProt YbgH pH 4.75" in FIG. 11).

In addition, 10 µl of purified saposin A were mixed with 1.6 µl of a 1% (w/v) LDAO-detergent solution and 2.6 µl of purified membrane protein YbgH (10 mg/ml, 20 mM Hepes pH 7.5, 150 mM NaCl, 5% glycerol, 0.03% (w/v) DDM, 0.5 mM TCEP) and incubated for 10 min at 37° C. Subsequently, 50.8 µl of GF-buffer pH 7.5 were added to the mixture to obtain a final reaction volume of 65 µl. After 10 min incubation at room temperature, the mixture was subjected to a gel-filtration step as above (cf. "Saposin+Detergent+MemProt YbgH pH 7.5" in FIG. 11).

Finally, 10 µl of purified saposin A were mixed with 1.6 µl of a 1% (w/v) LDAO-detergent solution and 2.6 µl of purified membrane protein YbgH (10 mg/ml, 20 mM Hepes pH 7.5, 150 mM NaCl, 5% glycerol, 0.03% (w/v) DDM, 0.5 mM TCEP) and incubated for 10 min at 37° C. Subsequently, 50.8 µl GF-buffer pH 4.75 were added to the mixture to obtain a final reaction volume of 65 µl. After 10 min incubation at room temperature, the mixture was subjected to a gel-filtration step as above, using GF-buffer 4.75 (cf. "Saposin+Detergent+MemProt YbgH pH 4.75" in FIG. 11).

The results, which are depicted in FIG. 11, demonstrate that the process for preparing Salipro particles according to the invention allows for additional incorporation of membrane proteins into the particles (cf. Example 5). The elution profile of Salipro-YbgH (cf. "Saposin+Detergent+Lipids+MemProt YbgH pH 7.5" in FIG. 11) displays two major peaks, with the first peak at an elution volume of 1.5 ml corresponding to the membrane protein incorporated into Salipro particles and the second peak at 1.8 ml corresponding to lipid-only Salipro-particles, eluting at the same volume as has been observed before (cf. FIG. 10, lipid-only Salipro-particles). With the method according to the invention, saposin A, lipids and the membrane protein self-assemble into water-soluble, lipid-protein particles with the membrane protein incorporated therein.

In addition, the results demonstrate that also the process for generating Salipro particles comprising hydrophobic agents according to the invention requires the presence of lipids (cf. Example 5 and "Saposin+Detergent+Lipids+MemProt YbgH pH 7.5" in FIG. 11 and Comparative Example 5 and "Saposin+Detergent+MemProt YbgH pH 7.5" in FIG. 11) and fails to yield stable particles at a lysosomal pH of 4.75 (cf. Comparative Example 5 and "Saposin+Detergent+MemProt YbgH pH 4.75" in FIG. 11). In the absence of lipids (cf. Comparative Example 5 and "Saposin+Detergent+MemProt YbgH pH 7.5" in FIG. 11), the elution profile corresponded to that of purified saposin A with an ascending shoulder, the latter of which is most likely formed by YbgH alone.

Example 6

Salipro particles comprising another prokaryotic membrane protein, the MATE transporter, were prepared (Salipro-MATE, cf. "Saposin+Detergent+Lipids+MemProt MATE" in FIG. 12).

10 µl of purified saposin A (1.2 mg/ml, 20 mM Hepes pH 7.5, 150 mM NaCl) were mixed with 2 µl of a 1% (w/v) DDM-detergent solution, 5 µl of a brain-lipid solution (5 mg/ml brain lipids, Sigma-Aldrich; 50 mM Hepes pH 7.5, 150 mM NaCl, 0.28% (w/v) DDM) and 7 µl of purified membrane protein MATE (9 mg/ml, 20 mM Hepes pH 7.5, 150 mM NaCl, 5% glycerol, 0.01% DMNG, 0.5 mM TCEP) and incubated for 10 min at 37° C. Subsequently, 41 µl GF-buffer pH 7.5 were added to the mixture to obtain a final reaction volume of 65 µl. After 10 min incubation at room temperature, the mixture was subjected to a gel-filtration step on a Superdex™ 200 5/150 GL analytical gel filtration column using a ÄKTAmicro™ chromatography system (both GE Healthcare) equipped with the Autosampler A-905, which automatically injected 25 µl of protein containing sample. Analytical gel filtration runs were performed at 4° C. at a flow rate of 0.2 ml/min in GF-buffer 7.5 (cf. "Saposin+Detergent+Lipids+MemProt MATE" in FIG. 12).

Comparative Example 6

10 µl of purified saposin A were mixed with 2 µl of a 1% (w/v) DDM-detergent solution and 7 µl of purified membrane protein MATE (9 mg/ml, 20 mM Hepes pH 7.5, 150 mM NaCl, 5% glycerol, 0.01% DMNG, 0.5 mM TCEP) and incubated for 10 min at 37° C. Subsequently, 46 µl GF-buffer pH 7.5 were added to the mixture to obtain a final reaction volume of 65 µl. After 10 min incubation at room temperature, the mixture was subjected to a gel-filtration step as above (cf. "Saposin+Detergent+MemProt MATE" in FIG. 12).

As lipid-only Salipro particle control, 10 µl of purified saposin A were mixed with 2 µl DDM-detergent (1% w/v), 5 µl of a brain-lipid solution and incubated for 10 min at 37° C. Subsequently, 48 µl GF-buffer pH 7.5 were added to the mixture to obtain a final reaction volume of 65 µl. After 10 min incubation at room temperature, the mixture was subjected to a gel-filtration step as above (cf. "Saposin+Detergent+Lipids in FIG. 12).

As negative control, 10 µl of purified saposin A were incubated for 10 min at 37° C. Subsequently, 55 µl GF-buffer pH 7.5 was added to the mixture to obtain a final reaction volume of 65 µl. After 10 min incubation at room temperature, the mixture was subjected to a gel-filtration step, as above (cf. "Saposin" in FIG. 12).

The results, which are depicted in FIG. 12, demonstrate that also the prokaryotic membrane transporter MATE could easily be incorporated into Salipro particles by following the method of the invention. The elution profile of Salipro-MATE (cf. Example 6 and "Saposin+Detergent+Lipids+MemProt MATE" in FIG. 12) displays one major peak at 1.5 ml elution volume, corresponding to the membrane protein incorporated into Salipro particles and a smaller, lower molecular weight peak at 1.8 ml elution volume, corresponding to lipid-only Salipro-particles, eluting at the same volume as the lipid-only Salipro-particles (cf lipid-only Salipro particle control "Saposin+Detergent+Lipids" and cf. FIG. 10).

Example 7

Figure 13:
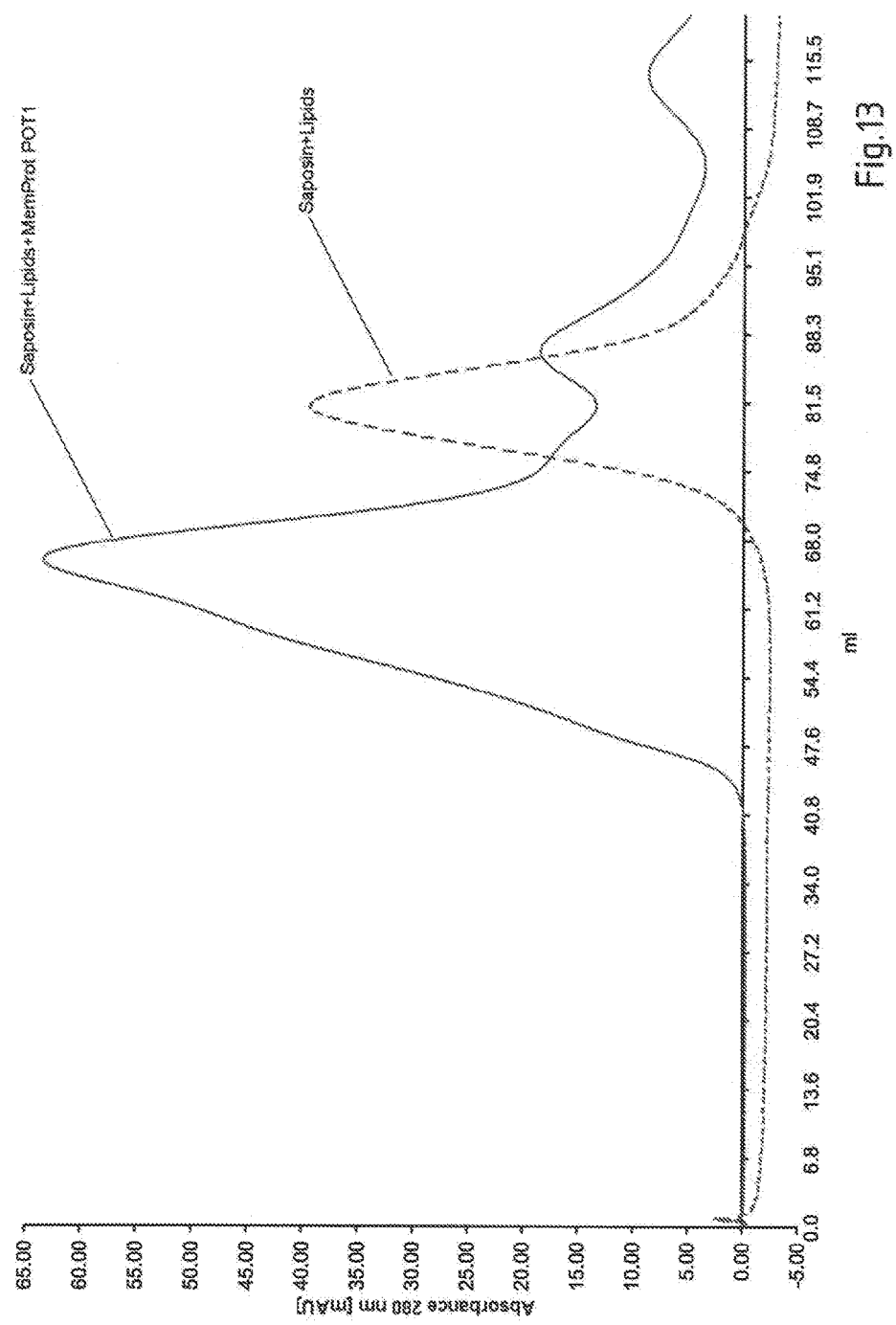
FIG. 13 is a gel filtration elution profile of Salipro particles ("Saposin+Lipids") or Salipro particles comprising the homotetrameric membrane protein POT1 ("Saposin+Lipids+MemProt POT1") according to the invention as described in Example 7.

Salipro particles comprising another prokaryotic membrane protein, the *S. oenidensis* peptide transporter POT1, were prepared (Salipro-POT1, cf. "Saposin+Lipids+MemProt POT1" in FIG. 13).

230 µl of a brain-lipid solution (5 mg/ml brain lipids, Sigma-Aldrich; 50 mM Hepes pH 7.5, 150 mM NaCl, 0.28% (w/v) DDM) were incubated for 10 min at 37° C., supplemented with 250 µl of purified membrane protein POT1 (10 mg/ml, 20 mM Hepes pH 7.5, 150 mM NaCl, 5% glycerol, 0.3% NM, 0.5 mM TCEP) and incubated for 30 s at 37° C. Subsequently, 460 µl of purified saposin A (1.2 mg/ml, 20 mM Hepes pH 7.5, 150 mM NaCl) were added, incubated for 1 min at 37° C., supplemented with 630 µl GF-buffer pH 7.5. After 10 min incubation at RT, 2 ml of GF-buffer pH 7.5 were added and the sample was centrifuged for 2 min at 14000 rpm. The supernatant was subjected to a gel-filtration step on a HiLoad Superdex™ 200 16/60 GL column using an ÄKTAexplorer™ 10 chromatography system (both GE Healthcare) using GF-buffer 7.5 (cf. "Saposin+Lipids+MemProt POT1" in FIG. 13).

The experiment was performed again as described in the previous paragraph, with the exception that no POT 1 was added (cf. "Saposin+Lipids" in FIG. 13).

The elution profile of Salipro-POT1 displays one major peak corresponding to the membrane protein incorporated into Salipro particles and a smaller, lower molecular weight peak corresponding to lipid-only Salipro-particles. Accordingly, saposin A, lipids and the membrane protein associated in such way to form water-soluble particles with an incorporated membrane protein.

Example 8

Figure 14:
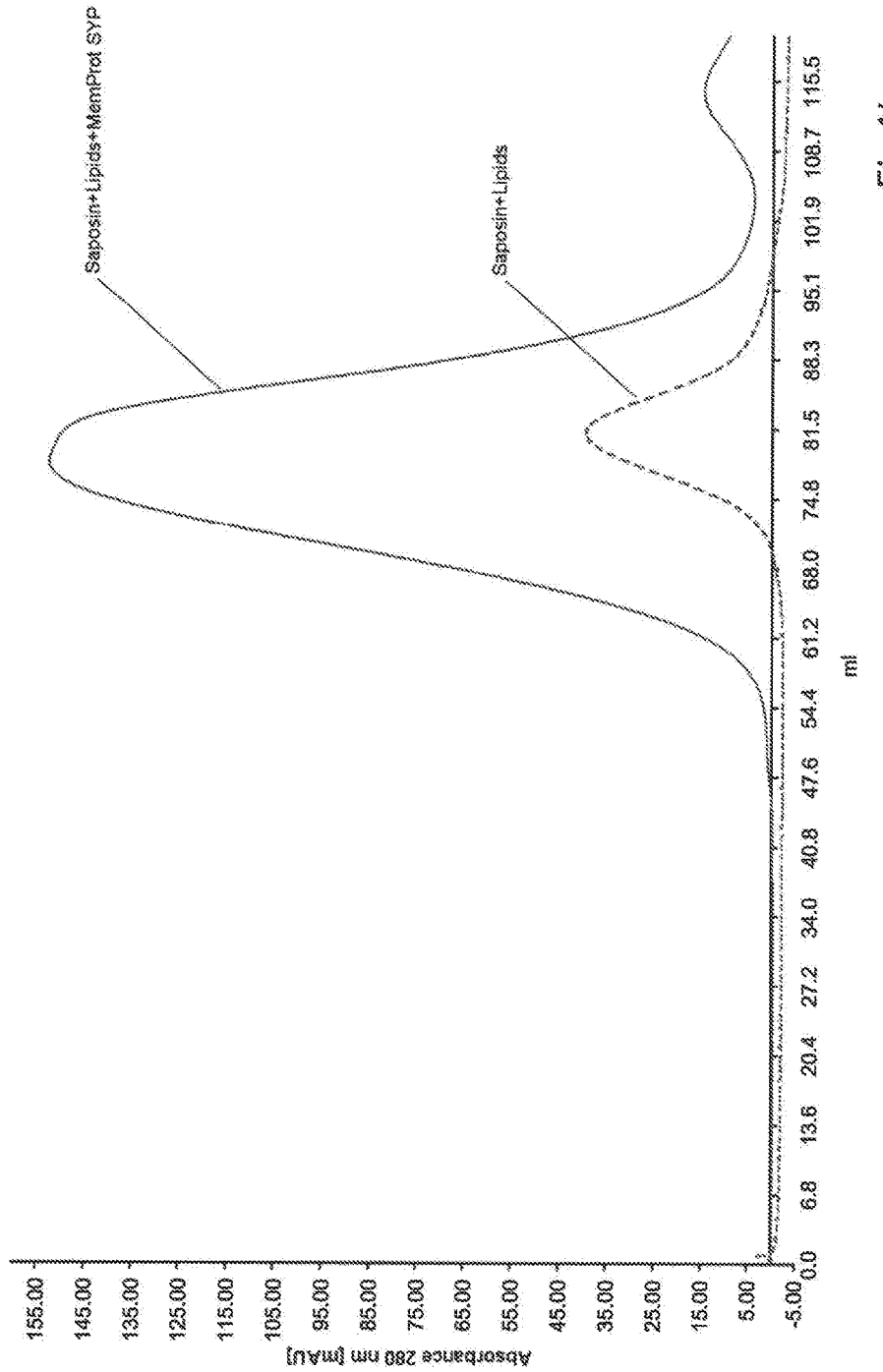
FIG. 14 is a gel filtration elution profile of Salipro particles ("Saposin+Lipids") or Salipro particles comprising the human membrane protein Synaptophysin ("Saposin+Lipids+MemProt SYP") according to the invention as described in Example 8.

Salipro particles comprising eukaryotic membrane protein, purified human Synaptophysin (SYP), were prepared (Salipro-SYP, cf. "Saposin+Lipids+MemProt SYP" in FIG. 14).

500 µl of a brain-lipid solution (5 mg/ml brain lipids, Sigma-Aldrich; 50 mM Hepes pH 7.5, 150 mM NaCl, 0.28% (w/v) DDM) were incubated for 10 min at 37° C., supplemented with 800 µl of purified membrane protein SYP (4.2 mg/ml, 20 mM Hepes pH 7.5, 150 mM NaCl, 5% glycerol, 0.03% (w/v) DDM) and incubated for 5 min at 37° C. Then, 900 µl of purified saposin A (1.2 mg/ml, 20 mM Hepes pH 7.5, 150 mM NaCl) were added, incubated for 1 min at 37° C., supplemented with 900 µl GF-buffer pH 7.5. After 10 min incubation at RT, 1.9 ml of GF-buffer pH 7.5 were added and the sample was centrifuged for 2 min at 14000 rpm. The supernatant was subjected to a gel-filtration step on a HiLoad Superdex™ 200 16/60 GL column using an ÄKTAexplorer™ 10 chromatography system (both GE Healthcare) using GF-buffer 7.5 (cf. "Saposin+Lipids+MemProt SYP" in FIG. 14).

230 µl of a brain-lipid solution (5 mg/ml brain lipids, Sigma-Aldrich; 50 mM Hepes pH 7.5, 150 mM NaCl, 0.28% (w/v) DDM) were incubated for 10 min at 37° C. Then, 460 µl of purified saposin A (1.2 mg/ml, 20 mM Hepes pH 7.5, 150 mM NaCl) were added, the mixture was incubated for 1 min at 37° C. and subsequently diluted with 630 µl GF-buffer pH 7.5. After 10 min incubation at RT, 2 ml of GF-buffer pH 7.5 were added and the sample was centrifuged for 2 min at 14000 rpm. The supernatant was subjected to a gel-filtration step on a HiLoad Superdex™ 200 16/60 GL column using an ÄKTAexplorer™ 10 chromatography system (both GE Healthcare) using GF-buffer 7.5 (cf. "Saposin+Lipids" in FIG. 14).

Salipro-SYP elutes as a single peak with a minor descending shoulder indicating the presence of lipid-only Salipro particles at that position (cf. "Saposin+Lipids+MemProt SYP" and "Saposin+Lipids" in FIG. 14).

V

Salipro Particles Comprising Hydrophobic Organic Compounds

In order to assess the capability of Salipro particles as carriers for hydrophobic compounds, such as lipophilic drugs, it was evaluated whether it would be possible to incorporate such compounds into the Salipro particles of the invention by using the same approach as described above for incorporation of membrane proteins, i.e. mixing purified saposin A with lipids and the compound to be incorporated at physiological pH with a subsequent gel filtration step.

Example 9

Curcumin was used as hydrophobic model drug for testing incorporation into Salipro particles using the method of the invention. Curcumin was primarily chosen because of its various pharmacologic implications (such as anti-cancer, anti-inflammatory, anti-oxidant and anti-proliferative activity) and its fluorescence in lipid environments. Using its UV-absorbance and fluorescence characteristics (excitation 420 nm, emission 500 nm) in a lipid environment, incorporation of Curcumin into Salipro particles can easily be followed.

1 µl of Curcumin (10 mg/ml, in DMSO) was mixed with 60 µl of a brain-lipid solution (5 mg/ml brain lipids, Sigma-Aldrich; 50 mM Hepes pH 7.5, 150 mM NaCl, 0.28% (w/v) DDM) and incubated for 15 min at 37° C. Subsequently, 100 µl of purified saposin A (1.2 mg/ml, 20 mM Hepes pH 7.5, 150 mM NaCl) were added, incubated for 10 min at 37° C. and 89 µl GF-buffer pH 7.5 added, followed by incubation of the mixture for 10 min at RT. Then, 250 µl of GF-buffer pH 7.5 were added and the sample was subjected to a gel-filtration step on a Superdex™ 200 10/300 GL column using an ÄKTAexplorer™ 10 chromatography system (both GE Healthcare) using GF-buffer 7.5. UV absorbance was measured at 280 nm (protein) and at 420 nm (Curcumin), cf. "Salipro-Curcumin" in FIG. 15.

Figure 15:
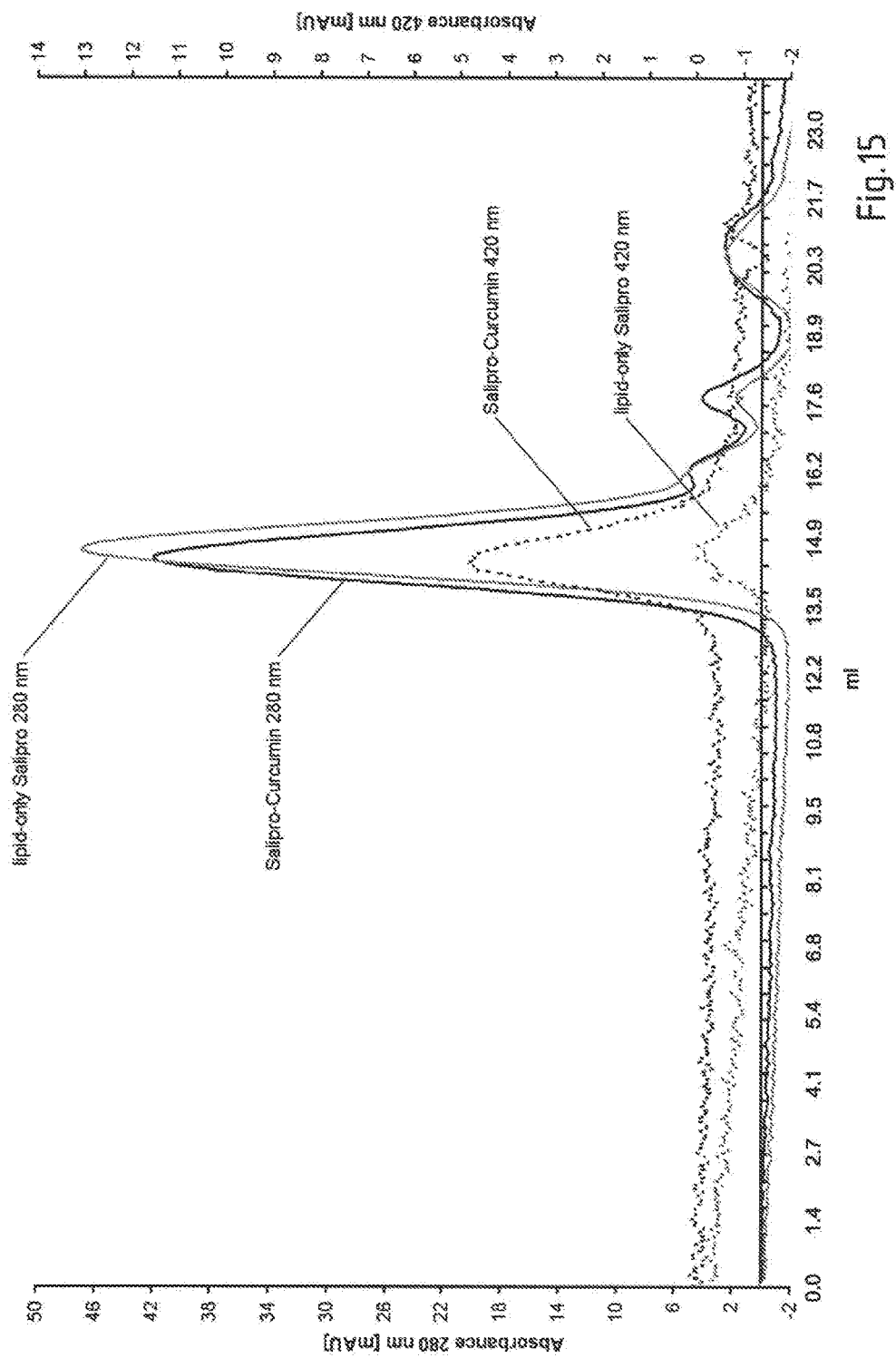
FIG. 15 is a gel filtration elution profile of Salipro particles ("lipid-only Salipro") or Salipro particles comprising the lipophilic drug Curcumin ("Salipro-Curcumin") according to the invention as described in Example 9.

The experiment was performed again as described in the previous paragraph, with the exception that no Curcumin was added (cf. "Lipid-only Salipro" in FIG. 15).

The results, which are depicted in FIG. 15, demonstrate that it is possible to incorporate Curcumin into the Salipro particles of the invention, as indicated by the presence of both an absorption peak at 280 nm and a fluorescence peak at the exact position where the characteristic Salipro-protein absorption peak is present, while lipid-only Salipro particles exhibit only a minute fluorescence peak (cf. "Lipid-only Salipro" in FIG. 15). Similar results were obtained when Curcumin emission at 500 nm was recorded. At 280 nm, purified Salipro-Curcumin particles exhibit a monodisperse peak which is almost identical to lipid-only Salipro particles (cf. "Salipro-Curcumin" and "Lipid-only Salipro" in FIG. 15).

Further experiments demonstrated that, in the absence of saposin A, a mixture comprising lipids and Curcumin is not capable of self-assembling into soluble lipid-Curcumin complexes. Salipro particles of the invention are capable of rendering otherwise insoluble lipophilic compounds soluble, by incorporation into the lipid environment of the Salipro nanoscale particles.

VI

Salipro Particles Adjust to the Size/nature of the Incorporated Molecules

Example 10

The results of example 4 above indicated that the Salipro particles obtainable by the method of the invention are inherently flexible in size (cf. the effect of the different lipids used in the preparation of the particles in FIG. 10). This could be confirmed in subsequent experiments using increasing amounts of lipids in the preparation of the Salipro particles according to the method of the invention.

Varying amounts ("Lipids 5": 1 µl, "Lipids 12.5": 2.5 µl, "Lipids 25": 5 µl, "Lipids 50": 10 µl, "Lipids 100": 20 µl) of a brain-lipid solution (5 mg/ml brain lipids, Sigma-Aldrich; 50 mM Hepes pH 7.5, 150 mM NaCl, 0.28% (w/v) DDM) were incubated for 10 min at 37° C. 10 µl of purified saposin A were added, incubated for 1 min at 37° C. and GF-buffer pH 7.5 was added to a final volume of 41 µl. After 10 min incubation at RT, 24 µl of GF-buffer pH 7.5 were added and the samples were subjected to a gel-filtration step on a Superdex™ 200 5/150 GL analytical gel filtration column using a ÄKTAmicro™ chromatography system (both GE Healthcare) equipped with the Autosampler A-905, which automatically injected 25 µl of protein containing sample. Analytical gel filtration runs were performed at 4° C. at a flow rate of 0.2 ml/min in GF-buffer 7.5 (cf. "Saposin+Lipids 5", "Saposin+Lipids 12.5", "Saposin+Lipids 25", "Saposin+Lipids 50", "Saposin+Lipids 100" in FIG. 16).

As negative control, 10 µl of purified saposin A (1.2 mg/ml, 20 mM Hepes pH 7.5, 150 mM NaCl) were incubated for 1 min at 37° C. and 31 µl GF-buffer pH 7.5 were added. After 10 min incubation at RT, 24 µl of GF-buffer pH 7.5 were added and the sample was subjected to a gel-filtration step on a Superdex™ 200 5/150 GL analytical gel filtration column using a ÄKTAmicro™ chromatography system (both GE Healthcare) equipped with the Autosampler A-905, which automatically injected 25 µl of protein containing sample. Analytical gel filtration runs were performed at 4° C. at a flow rate of 0.2 ml/min in GF-buffer 7.5 (cf. "Saposin" in FIG. 16).

Figure 16:
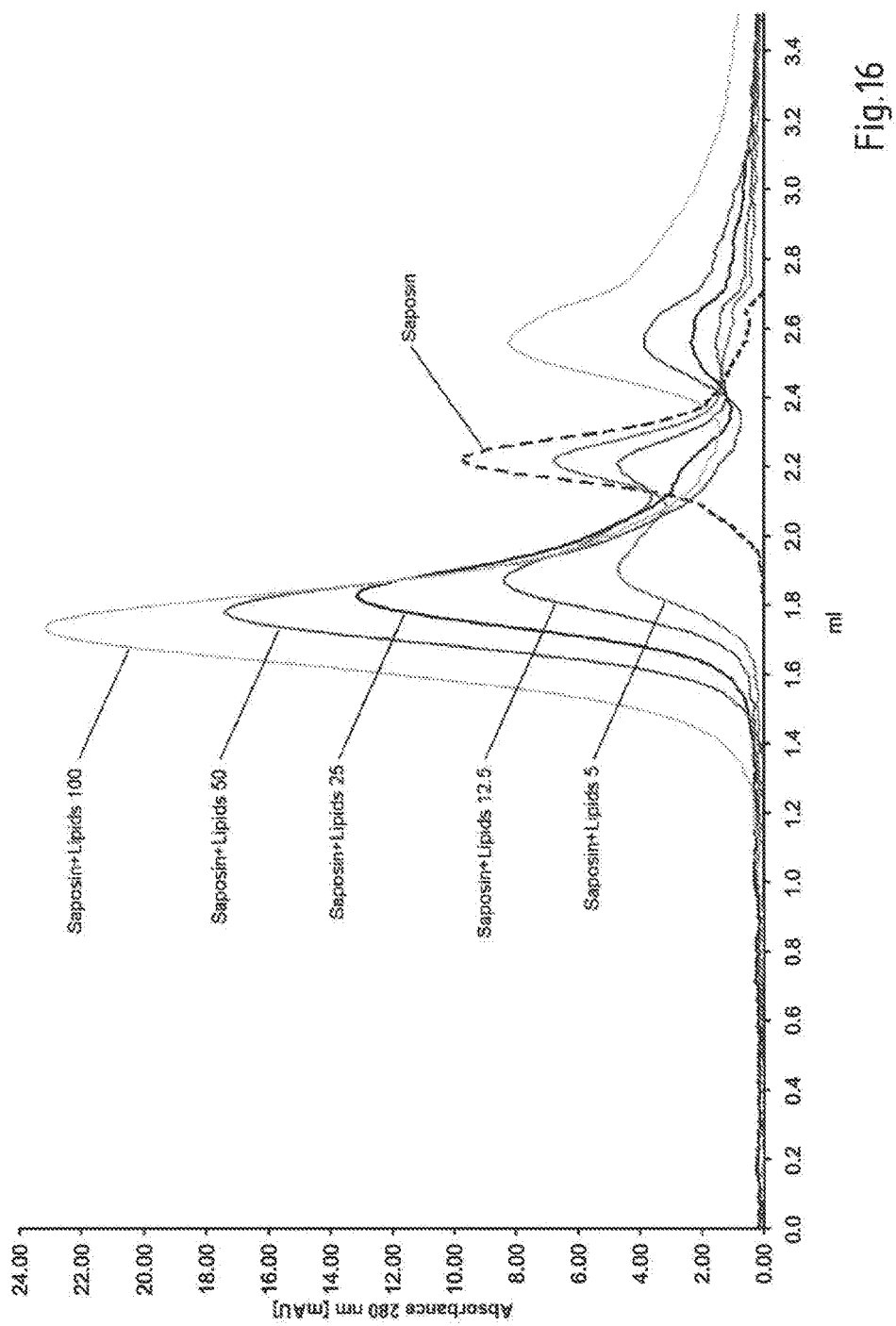
FIG. 16 is a gel filtration elution profile of Salipro particles ("lipid-only Salipro") according to the invention that were prepared with varying amounts of lipids as described in Example 10.

The results, which are depicted in FIG. 16, demonstrate that the Salipro particles obtainable with the method of the invention are flexible in size, whereby the size can be controlled, for example, by the amount of lipids added during preparation of the particles.

Example 11

The inherent flexibility in Salipro particle size also becomes apparent from experiments in which differently sized membrane proteins are incorporated into Salipro particles of the invention.

Salipro particles comprising small (27 kDa) human Synaptophysin (Saposin-SYP), the tetrameric (4×56 kDa) E. coli peptide transporter POT1 (Saposin-POT1) and lipid-only Salipro particles were prepared as described in Examples 7 and 8. The samples were subjected to gel filtration on a HiLoad Superdex™ 200 16/60 GL column using an ÄKTAexplorer™ 10 chromatography system (both GE Healthcare) with GF-buffer 7.5.

Figure 17:
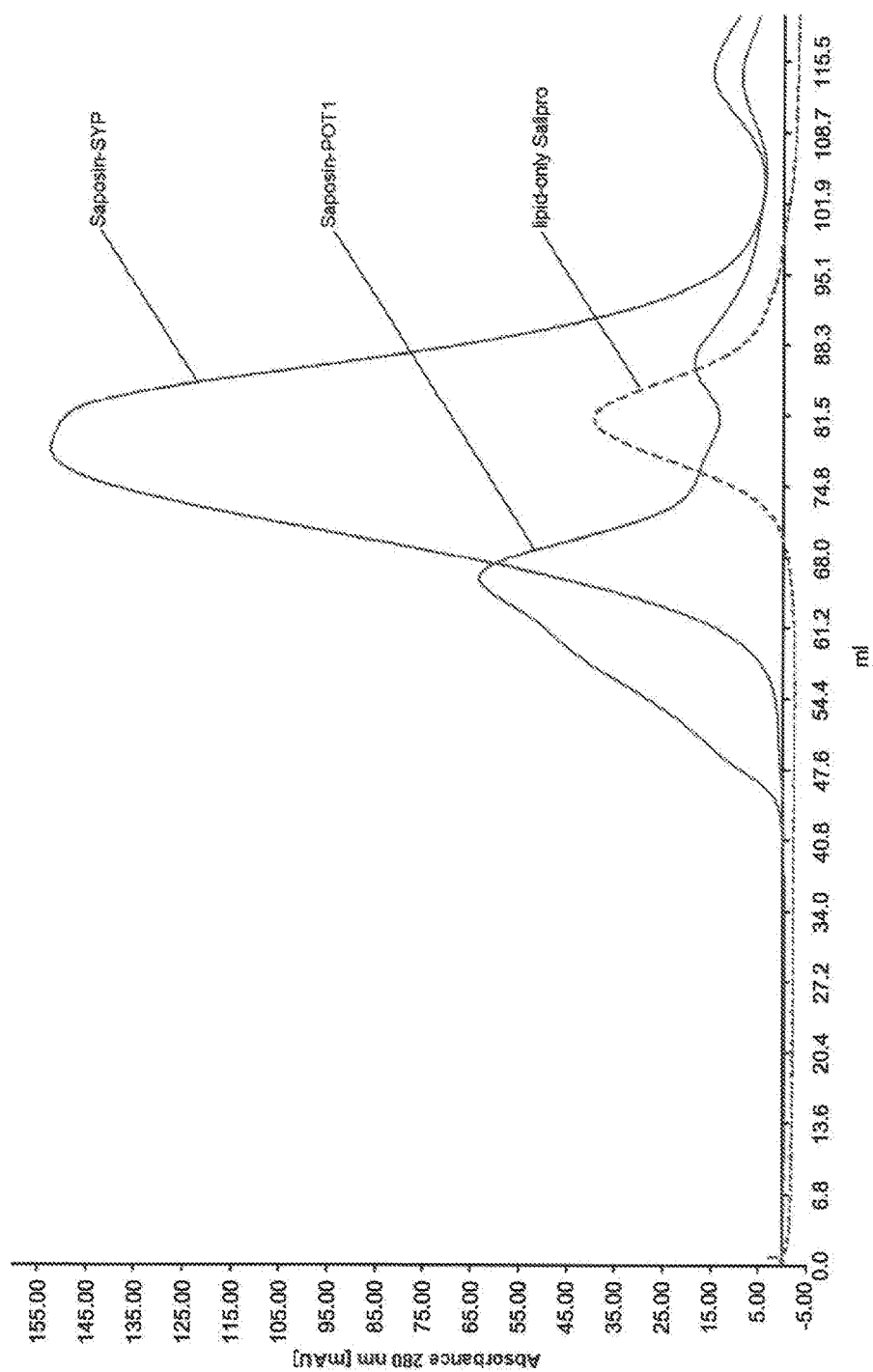
FIG. 17 is a gel filtration elution profile of Salipro particles ("lipid-only Salipro") and Salipro particles comprising POT1 or Synaptophysin ("Saposin-POT1"; "Saposin-SYP") according to the invention as described in Example 11.

As evident from the comparison of the elution profiles in FIG. 17, the size of the Salipro particles of the invention is flexible and seems to adjust to the size of the hydrophobic agent incorporated therein. Whereas the "empty", i.e. lipid-only, Salipro particles have an average hydrodynamic radius of about 3 nm, Salipro particles comprising the oligomeric POT1 transporter, expand showing an average hydrodynamic radius of about 10 nm.

VII

Visualization of Salipro Particles

Salipro particles with the incorporated bacterial peptide transporter (Salipro-POT1) were prepared as described in Example 7 and analyzed with negative-stain electron microscopy.

Example 12

Figure 18:
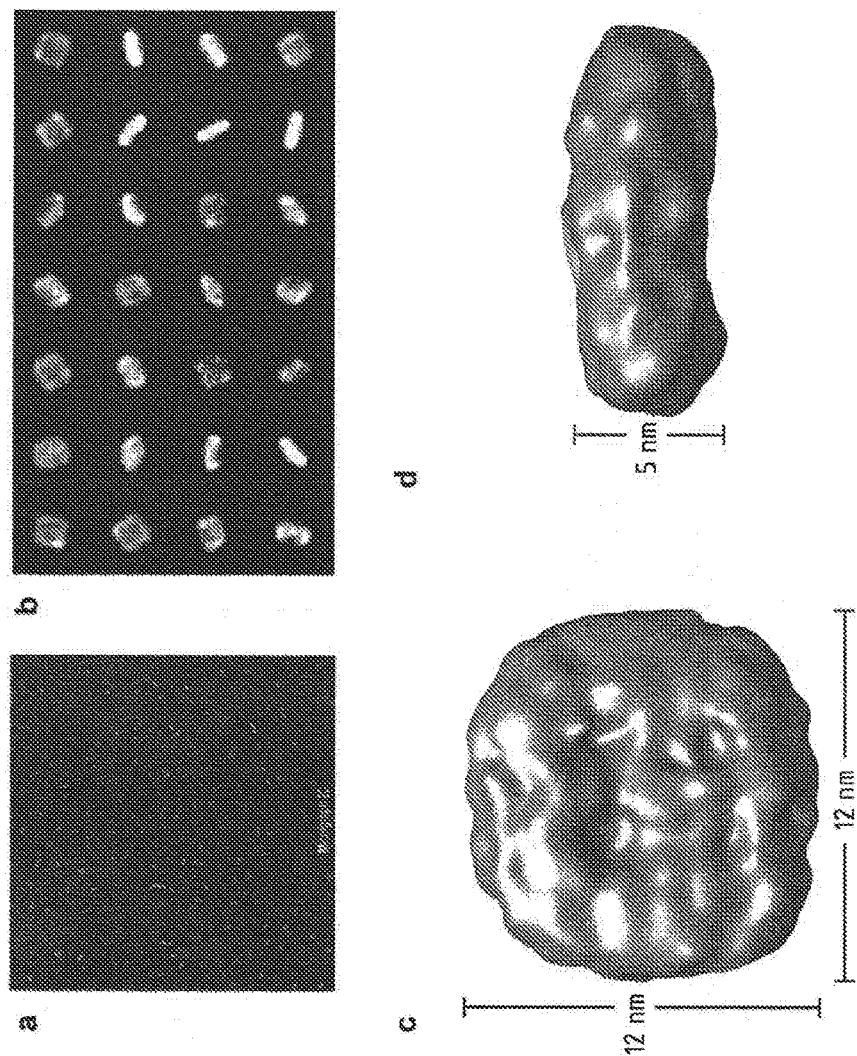
FIG. 18 shows single particle analysis of Salipro-POT1 particles with negative-stain electron microscopy as described in Example 12, wherein a) depicts an electron micrograph and b) class averages of Salipro-POT1 particles. Inlets c) and d) show surface rendered 3D reconstruction of Salipro-POT1 in top and side view respectively.

Samples of Salipro-POT1 were applied to glow-discharged copper grids coated with a thin carbon film and stained with uranyl formate. Imaging was performed using a JEOL JEM2100F electron microscope at an acceleration voltage of 200 kV. Micrographs were recorded on a 4 k CCD camera. An exemplary electron micrograph of purified Salipro-POT1 is shown in FIG. 18 a). Salipro-POT resembles a generally square-shaped particle that adopts various orientations on the grid, i.e. various side- or top-/bottom views of the particle were visible, allowing for 3D single-particle reconstruction.

Single Salipro-POT1 particles were picked from micrographs and processed using the EMAN2 suite. For the 3D-reconstruction, no symmetry was used. FIG. 18 b) depicts class averages of the particles and FIGS. 18 c) and d) surface rendered 3D reconstruction of Salipro-POT1, in top view and side view, respectively.

The appearance and the dimensions of the square-shaped Salipro-POT1 disc are in good agreement with the homotetrameric membrane protein complex formed by the bacterial peptide transporter POT1 in its native bacterial membrane environment. The thickness of the disc is about 5 nm, which is reminiscent of the dimensions of a lipid bilayer and in accordance with expectations from the known structure of POT1 which mainly consists of transmembrane helices and lacks large cytosolic domains. The diameters and maximum diameter (major axis length) are in the range of 12 nm ÷ 2 nm. Given the size and the apparent stoichiometry of the Salipro-POT1 particles, each particle seems to be composed of four POT1 proteins and four saposin A molecules. This indicates a certain flexibility of saposin A to assemble into homogenous and stable lipoprotein-complexes, by adapting to the size of the incorporated hydrophobic agent.

Salipro particles may therefore be composed of two saposin A molecules surrounding a lipid/detergent core in the empty, lipid-only state or when loaded with low-molecular weight and/or monomeric hydrophobic agents (cf. FIGS. 2 to 4 and 6 to 7), as well as several saposin A molecules around larger hydrophobic lipid/protein assemblies, as is the case for example with the homotetrameric POT1 (cf. FIGS. 5 and 18).

VIII

Stability of Salipro Particles

As demonstrated by the examples above, Salipro particles are capable of incorporating a variety of lipids, membrane proteins and hydrophobic compounds at physiological pH, giving rise to nanoscale complexes that are soluble in an aqueous environment. To confirm practical applicability of the Salipro particles of the invention, their respective stability over time, temperature and various treatment conditions was tested.

Example 13

To assess thermostability, samples of lipid-only Salipro particles (65 ul each), prepared as described in Example 7 above, were flash-frozen, stored at −80° C., thawed and incubated at either 0° C., 37° C., 50° C., 73° C. or 95° C. for 10 min. The subsequent analysis was performed via a gel-filtration step on a Superdex™ 200 5/150 GL analytical gel filtration column using a ÄKTAmicro™ chromatography system (both GE Healthcare) equipped with the Autosampler A-905, which automatically injected 25 µl of protein containing sample. Analytical gel filtration runs were performed at 4° C. at a flow rate of 0.2 ml/min in GF-buffer 7.5.

The results, which are depicted in FIG. 19, demonstrate that the Salipro particles of the invention display a certain thermostability.

Further experiments revealed that the Salipro particles of the invention are also robust over concentrating using standard centrifugal filter units, freezing and thawing. In addition, it is possible to freeze-dry, store and re-hydrate the Salipro particles without significant quality deterioration.

The invention claimed is:

1. A disc-shaped particle comprising
a lipid binding polypeptide, lipids and a hydrophobic agent,
wherein the particle does not comprise a hydrophilic or aqueous core,
wherein the hydrophobic agent is neither a lipid nor a detergent, and
wherein the lipid binding polypeptide is a
(a) "saposin-like protein" (SAPLIP) belonging to the SAPLIP family of lipid interacting proteins, characterized by a saposin fold, wherein the saposin fold comprises a conserved alpha-helical three-dimensional structure that is stabilized by highly conserved intramolecular disulphide bonds, or
(b) a derivative form thereof, wherein the derivative has the saposin fold, and comprises six cysteine residues corresponding to the six cysteines in the SAPLIP founding member saposin A (SEQ ID NO. 1) and is
(i) a protein having at least 80% sequence identity to the full length sequence of SEQ ID NO. 1, 2, 3, 4, 5 or 6;
(ii) a protein having at least 40% sequence identity to the full length sequence of SEQ ID NO. 1, 2, 3, 4, 5 or 6, wherein said protein is amphipathic, forms at least one alpha helix, and is capable of self-assembling together with solubilized lipids into lipoprotein particles when employed in the method comprising the steps of: A. contacting the protein with detergent-solubilized lipids in a liquid environment; and B. allowing for self-assembly of the particle at a pH of from 6.0 to 10.0; or
(iii) a protein comprising the sequence of SEQ ID NO. 1, 2, 3, 4, 5 or 6 in which 1 to 40 amino acids have been deleted, added, inserted and/or substituted.

2. The particle according to claim 1, wherein the particle has a maximum diameter of from 2 nm to 200 nm.

3. The particle according to claim 1, wherein the hydrophobic agent is selected from the group consisting of a hydrophobic organic compound and a hydrophobic biomolecule.

4. The particle according to claim 3, wherein the hydrophobic organic compound and/or the hydrophobic biomolecule is selected from the group consisting of a biologically active agent, a drug, an active ingredient of a drug, an active ingredient of a cosmetic product, an active ingredient of a plant protective product, a dietary and/or nutritional supplement, a diagnostic probe, a contrast agent, a label and an indicator.

5. The particle according to claim 3, wherein the hydrophobic biomolecule is a protein selected from the group consisting of a membrane protein, an integral transmembrane protein, an integral monotopic membrane protein, a peripheral membrane protein, an amphitropic protein in a lipid-bound state, a lipid-anchored protein and a chimeric protein with a fused hydrophobic and/or transmembrane domain.

6. The particle according to claim 1, wherein the lipids are lipid bilayer forming lipids and/or biocompatible lipids.

7. The particle according to claim 1, wherein the lipids are selected from the group consisting of eukaryotic lipids, phospholipids and/or lipids present in the white and grey matter of the brain.

8. The particle according to claim 1, wherein the lipid binding polypeptide is a chimeric polypeptide further comprising a functional moiety.

9. The particle according to claim 1, wherein the lipid binding polypeptide is saposin A or a derivative form thereof.

10. A process for preparing a disc-shaped particle comprising a lipid binding polypeptide and lipids, wherein the lipid binding polypeptide is
a) a "saposin-like protein" (SAPLIP) belonging to the SAPLIP family of lipid interacting proteins, characterized by a saposin fold, wherein the saposin fold comprises a conserved alpha-helical three-dimensional structure that is stabilized by highly conserved intramolecular disulphide bonds, or
b) a derivative form thereof wherein the derivative has the saposin fold, and comprises six cysteine residues corresponding to the six cysteines in the SAPLIP founding member saposin A (SEQ ID NO. 1) and is
(i) a protein having at least 80% sequence identity to the full length sequence of SEQ ID NO. 1, 2, 3, 4, 5 or 6;
(ii) a protein having at least 40% sequence identity to the full length sequence of SEQ ID NO. 1, 2, 3, 4, 5 or 6, wherein said protein is amphipathic, forms at least one alpha helix, and is capable of self-assembling together with solubilized lipids into lipoprotein particles when employed in the method comprising the steps of: A. contacting the protein with detergent-solubilized lipids in a liquid environment; and B. allowing for self-assembly of the particle at a pH of from 6.0 to 10.0; or
(iii) a protein comprising the sequence of SEQ ID NO. 1, 2, 3, 4, 5 or 6 in which 1 to 40 amino acids have been deleted, added, inserted and/or substituted, and wherein the particle does not comprise a hydrophilic or aqueous core,
the process comprising the steps of:
a) contacting the lipid binding polypeptide with detergent-solubilized lipids in a liquid environment;
b) allowing for the self-assembly of the particle at a pH of from 6.0 to 10.0.

11. The process according to claim 10, wherein step b) comprises diluting the mixture obtained in step a) with a liquid containing less amounts of detergent than the mixture obtained in step a).

12. The process according to claim 10, wherein the process comprises in step b) or as a subsequent step c) the purification of the particles by at least partial removal of free lipids and/or free lipid binding polypeptide, wherein optionally the purification is performed by chromatography; ultracentrifugation; dialysis; contacting with detergent-binding biobeads; use of concentrators; or affinity chromatography, magnetic beads and/or membrane/filters to remove unbound/non-incorporated lipids and/or hydrophobic compounds.

13. The process according to claim 10 for preparing a disc-shaped particle comprising
a lipid binding polypeptide, lipids and a hydrophobic agent,
wherein the particle does not comprise a hydrophilic or aqueous core,
wherein the hydrophobic agent is neither a lipid nor a detergent, and
wherein the lipid binding polypeptide is a
(a) "saposin-like protein" (SAPLIP) belonging to the SAPLIP family of lipid interacting proteins, characterized by a saposin fold, wherein the saposin fold comprises a conserved alpha-helical three-dimensional structure that is stabilized by highly conserved intramolecular disulphide bonds, or
(b) a derivative form thereof wherein the derivative has the saposin fold, and comprises six cysteine residues corresponding to the six cysteines in the SAPLIP founding member saposin A (SEQ ID NO. 1) and is
(i) a protein having at least 80% sequence identity to the full length sequence of SEQ ID NO. 1, 2, 3, 4, 5 or 6;
(ii) a protein having at least 40% sequence identity to the full length sequence of SEQ ID NO. 1, 2, 3, 4, 5 or 6, wherein said protein is amphipathic, forms at least one alpha helix, and is capable of self-assembling together with solubilized lipids into lipoprotein particles when employed in the method comprising the steps of: A. contacting the protein with detergent-solubilized lipids in a liquid environment; and B. allowing for self-assembly of the particle at a pH of from 6.0 to 10.0; or
(iii) a protein comprising the sequence of SEQ ID NO. 1, 2, 3, 4, 5 or 6 in which 1 to 40 amino acids have been deleted, added, inserted and/or substituted,
wherein in step a) the lipid binding polypeptide is contacted with lipids in a liquid environment comprising the hydrophobic agent that is to be incorporated into the particle, and optionally, wherein the hydrophobic agent is selected from the group consisting of a hydrophobic organic compound and a hydrophobic biomolecule, wherein optionally,
a) the hydrophobic organic compound and/or the hydrophobic biomolecule is selected from the group consisting of a biologically active agent, a drug, an active ingredient of a drug, an active ingredient of a cosmetic product, an active ingredient of a plant protective product, a dietary and/or nutritional supplement, a diagnostic probe, a contrast agent, a label and an indicator; or
b) wherein the hydrophobic biomolecule is a protein selected from the group consisting of a membrane protein, an integral transmembrane protein, an integral monotopic membrane protein, a peripheral membrane protein, an amphitropic protein in a lipid-bound state, a lipid-anchored protein and a chimeric protein with a fused hydrophobic and/or transmembrane domain.

14. A particle obtainable according to the process of claim 10.

15. A pharmaceutical composition for delivering a hydrophobic agent to an individual in need thereof, comprising a disc-shaped particle comprising a lipid binding polypeptide, lipids and a hydrophobic agent,
wherein the particle does not comprise a hydrophilic or aqueous core,
wherein the hydrophobic agent is neither a lipid nor a detergent, and
wherein the lipid binding polypeptide is a
(a) "saposin-like protein" (SAPLIP) belonging to the SAPLIP family of lipid interacting proteins, characterized by a saposin fold, the saposin fold comprising a conserved alpha-helical three-dimensional structure that is stabilized by highly conserved intramolecular disulphide bonds, or
(b) a derivative form thereof, wherein the derivative has the saposin fold, and comprises the six cysteine residues corresponding to the six cysteine residues in the SAPLIP founding member saposin A (SEQ ID NO. 1) and is
(i) a protein having at least 80% sequence identity to the full length sequence of SEQ ID NO. 1, 2, 3, 4, 5 or 6;
(ii) a protein having at least 40% sequence identity to the full length sequence of SEQ ID NO. 1, 2, 3, 4, 5 or 6, wherein said protein is amphipathic, forms at least one alpha helix, and is capable of self-assembling together with solubilized lipids into lipoprotein particles when employed in the method comprising the steps of: A. contacting the protein polypeptide with detergent-solubilized lipids in a liquid environment; and B. allowing for self-assembly of the particle at a pH of from 6.0 to 10.0; or (iii) a protein comprising the sequence of SEQ ID NO. 1, 2, 3, 4, 5 or 6 in which 1 to 40 amino acids have been deleted, added, inserted and/or substituted, wherein the hydrophobic agent is an active ingredient of and/or wherein in addition to the hydrophobic agent an active ingredient is present.

16. A method of treating or preventing a disease or condition in an individual in need thereof, the method comprising: administering to the individual, a therapeutically effective amount of a pharmaceutically acceptable composition comprising a disc-shaped particle comprising:

a lipid binding polypeptide, lipids and a hydrophobic agent, wherein the particle does not comprise a hydrophilic or aqueous core, wherein the hydrophobic agent is neither a lipid nor a detergent, and wherein the lipid binding polypeptide is a (a) "saposin-like protein" (SAPLIP) belonging to the SAPLIP family of lipid interacting proteins, characterized by a saposin fold, wherein the saposin fold comprises a conserved alpha-helical three-dimensional structure that is stabilized by highly conserved intramolecular disulphide bonds, or (b) a derivative form thereof, wherein the derivative has the saposin fold, and comprises six cysteine residues corresponding to the six cysteines in the SAPLIP founding member saposin A (SEQ ID NO. 1) and is (i) a protein having at least 80% sequence identity to the full length sequence of SEQ ID NO. 1, 2, 3, 4, 5 or 6;

(ii) a protein having at least 40% sequence identity to the full length sequence of SEQ ID NO. 1, 2, 3, 4, 5 or 6, wherein said protein is amphipathic, forms at least one alpha helix, and is capable of self-assembling together with solubilized lipids into lipoprotein particles when employed in a method comprising the steps of: A. contacting the protein with detergent-solubilized lipids in a liquid environment; and B. allowing for self-assembly of the particle at a pH of from 6.0 to 10.0; or (iii) a protein comprising the sequence of SEQ ID NO. 1, 2, 3, 4, 5 or 6 in which 1 to 40 amino acids have been deleted, added, inserted and/or substituted.

17. A disc-shaped particle for use in: manufacturing a hydrophobic agent delivery particle, drug development, drug screening, membrane protein analysis or formulating a vaccine composition, the disc-shaped particle comprising:

a lipid binding polypeptide, lipids and a hydrophobic agent, wherein the particle does not comprise a hydrophilic or aqueous core, wherein the hydrophobic agent is neither a lipid nor a detergent, and wherein the lipid binding polypeptide is a (a) "saposin-like protein" (SAPLIP) belonging to the SAPLIP family of lipid interacting proteins, characterized by a saposin fold, wherein the saposin fold comprises a conserved alpha-helical three-dimensional structure that is stabilized by highly conserved intramolecular disulphide bonds, or (b) a derivative form thereof, wherein the derivative has the saposin fold, and comprises six cysteine residues corresponding to the six cysteines in the SAPLIP founding member saposin A (SEQ ID NO. 1) and is (i) a protein having at least 80% sequence identity to the full length sequence of SEQ ID NO. 1, 2, 3, 4, 5 or 6;

(ii) a protein having at least 40% sequence identity to the full length sequence of SEQ ID NO. 1, 2, 3, 4, 5 or 6, wherein said protein is amphipathic, forms at least one alpha helix, and is capable of self-assembling together with solubilized lipids into lipoprotein particles when employed in a method comprising the steps of: A. contacting the protein with detergent-solubilized lipids in a liquid environment; and B. allowing for self-assembly of the particle at a pH of from 6.0 to 10.0; or (iii) a protein comprising the sequence of SEQ ID NO. 1, 2, 3, 4, 5 or 6 in which 1 to 40 amino acids have been deleted, added, inserted and/or substituted.

18. The particle according to claim 1, wherein the particle has a maximum diameter of from 3 nm to 150 nm.

19. The particle according to claim 1, wherein the particle has a maximum diameter of from 3 nm to 100 nm.

20. The particle according to claim 1, wherein the lipids are selected from the group consisting of phospholipids, glycosphingolipids, sterols, phosphatidylcholine, phosphatidylserine (PS), 2-oleoyl-1-palmitoyl-sn-glycero-3-phosphocholine (POPC), 2-oleoyl-1-palmitoyl-sn-glycero-3-glycerol (POPG), 2-oleoyl-1-palmitoyl-sn-glycero-3-phosphoethanolamine (POPE), diacylglycerol, cholesterol, sphingomyelin, galactosylceramide, gangliosides, phosphatidylinositols, sulphogalactoceramides and combinations thereof.

21. The particle according to claim 8, wherein the functional moiety is a targeting moiety or a bioactive moiety.

22. The particle according to claim 9, wherein the derivative form of saposin A comprises an amino acid sequence with at least 60% sequence identity to SEQ ID NO. 1.

23. The method according to claim 16, wherein administration of the pharmaceutically acceptable composition comprises administering the pharmaceutically acceptable composition to the individual that prevents, treats or lessens the severity of a disease in said individual.

24. The method according to claim 16, wherein the pharmaceutically acceptable composition is formulated for oral, rectal, parenteral, buccal, intracisternal, intravaginal, intraperitoneal, or topical administration.

25. The method according to claim 24, wherein the pharmaceutically acceptable composition is formulated into the form of a powder, an ointment, a solution, an aerosol, a capsule, a solid, or a dispersion.

26. The method according to claim 16, wherein the method of treating or preventing a disease or condition in an individual in need thereof comprises administering the pharmaceutically acceptable composition to the individual in a diagnostic method.

27. The method according to claim 16, wherein the method of treating or preventing a disease or condition in an individual in need thereof comprises administering the pharmaceutically acceptable composition to the individual in a cosmetic treatment.

* * * * *

```
                         SEQUENCE LISTING

<160> NUMBER OF SEQ ID NOS: 12

<210> SEQ ID NO 1
<211> LENGTH: 81
<212> TYPE: PRT
<213> ORGANISM: Homo sapiens

<400> SEQUENCE: 1

Ser Leu Pro Cys Asp Ile Cys Lys Asp Val Val Thr Ala Ala Gly Asp
1               5                   10                  15

Met Leu Lys Asp Asn Ala Thr Glu Glu Ile Leu Val Tyr Leu Glu
            20                  25                  30

Lys Thr Cys Asp Trp Leu Pro Lys Pro Asn Met Ser Ala Ser Cys Lys
        35                  40                  45

Glu Ile Val Asp Ser Tyr Leu Pro Val Ile Leu Asp Ile Ile Lys Gly
    50                  55                  60

Glu Met Ser Arg Pro Gly Glu Val Cys Ser Ala Leu Asn Leu Cys Glu
65                  70                  75                  80

Ser

<210> SEQ ID NO 2
<211> LENGTH: 79
<212> TYPE: PRT
<213> ORGANISM: Homo sapiens

<400> SEQUENCE: 2

Gly Asp Val Cys Gln Asp Cys Ile Gln Met Val Thr Asp Ile Gln Thr
1               5                   10                  15

Ala Val Arg Thr Asn Ser Thr Phe Val Gln Ala Leu Val Glu His Val
            20                  25                  30

Lys Glu Glu Cys Asp Arg Leu Gly Pro Gly Met Ala Asp Ile Cys Lys
        35                  40                  45

Asn Tyr Ile Ser Gln Tyr Ser Glu Ile Ala Ile Gln Met Met Met His
    50                  55                  60

Met Gln Pro Lys Glu Ile Cys Ala Leu Val Gly Phe Cys Asp Glu
65                  70                  75
```

<210> SEQ ID NO 3
<211> LENGTH: 80
<212> TYPE: PRT
<213> ORGANISM: Homo sapiens

<400> SEQUENCE: 3

Asp Val Tyr Cys Glu Val Cys Glu Phe Leu Val Lys Glu Val Thr Lys
1               5                   10                  15

Leu Ile Asp Asn Asn Lys Thr Glu Lys Glu Ile Leu Asp Ala Phe Asp
            20                  25                  30

Lys Met Cys Ser Lys Leu Pro Lys Ser Leu Ser Glu Glu Cys Gln Glu
        35                  40                  45

Val Val Asp Thr Tyr Gly Ser Ser Ile Leu Ser Ile Leu Leu Glu Glu
    50                  55                  60

Val Ser Pro Glu Leu Val Cys Ser Met Leu His Leu Cys Ser Gly Thr
65                  70                  75                  80

<210> SEQ ID NO 4
<211> LENGTH: 78
<212> TYPE: PRT
<213> ORGANISM: Homo sapiens

<400> SEQUENCE: 4

Gly Phe Cys Glu Val Cys Lys Lys Leu Val Gly Tyr Leu Asp Arg Asn
1               5                   10                  15

Leu Glu Lys Asn Ser Thr Lys Gln Glu Ile Leu Ala Ala Leu Glu Lys
            20                  25                  30

Gly Cys Ser Phe Leu Pro Asp Pro Tyr Gln Lys Gln Cys Asp Gln Phe
        35                  40                  45

Val Ala Glu Tyr Glu Pro Val Leu Ile Glu Ile Leu Val Glu Val Met
    50                  55                  60

Asp Pro Ser Phe Val Cys Leu Lys Ile Gly Ala Cys Pro Ser
65                  70                  75

<210> SEQ ID NO 5
<211> LENGTH: 145
<212> TYPE: PRT
<213> ORGANISM: Homo sapiens

<400> SEQUENCE: 5

Met Ala Thr Trp Ala Leu Leu Leu Ala Ala Met Leu Leu Gly Asn
1               5                   10                  15

Pro Gly Leu Val Phe Ser Arg Leu Ser Pro Glu Tyr Tyr Asp Leu Ala
            20                  25                  30

Arg Ala His Leu Arg Asp Glu Glu Lys Ser Cys Pro Cys Leu Ala Gln
        35                  40                  45

Glu Gly Pro Gln Gly Asp Leu Leu Thr Lys Thr Gln Glu Leu Gly Arg
    50                  55                  60

Asp Tyr Arg Thr Cys Leu Thr Ile Val Gln Lys Leu Lys Lys Met Val
65                  70                  75                  80

Asp Lys Pro Thr Gln Arg Ser Val Ser Asn Ala Ala Thr Arg Val Cys
            85                  90                  95

Arg Thr Gly Arg Ser Arg Trp Arg Asp Val Cys Arg Asn Phe Met Arg
        100                 105                 110

Arg Tyr Gln Ser Arg Val Thr Gln Gly Leu Val Ala Gly Glu Thr Ala
    115                 120                 125

Gln Gln Ile Cys Glu Asp Leu Arg Leu Cys Ile Pro Ser Thr Gly Pro
        130                 135                 140

Leu
145

<210> SEQ ID NO 6
<211> LENGTH: 129
<212> TYPE: PRT
<213> ORGANISM: Sus scrofa

<400> SEQUENCE: 6

Pro Gly Leu Ala Phe Ser Gly Leu Thr Pro Glu His Ser Ala Leu Ala
1               5                   10                  15

Arg Ala His Pro Cys Asp Gly Glu Gln Phe Cys Gln Asn Leu Ala Pro
            20                  25                  30

Glu Asp Pro Gln Gly Asp Gln Leu Leu Gln Arg Glu Leu Gly Leu
        35                  40                  45

Ile Cys Glu Ser Cys Arg Lys Ile Ile Gln Lys Leu Glu Asp Met Val
    50                  55                  60

Gly Pro Gln Pro Asn Glu Asp Thr Val Thr Gln Ala Ala Ser Arg Val
65                  70                  75                  80

Cys Asp Lys Met Lys Ile Leu Arg Gly Val Cys Lys Lys Ile Met Arg
                85                  90                  95

Thr Phe Leu Arg Arg Ile Ser Lys Asp Ile Leu Thr Gly Lys Lys Pro
            100                 105                 110

Gln Ala Ile Cys Val Asp Ile Lys Ile Cys Lys Glu Lys Thr Gly Leu
        115                 120                 125

Ile

<210> SEQ ID NO 7
<211> LENGTH: 4
<212> TYPE: PRT
<213> ORGANISM: Homo sapiens

<400> SEQUENCE: 7

Gly Asp Ser Leu
1

<210> SEQ ID NO 8
<211> LENGTH: 4
<212> TYPE: PRT
<213> ORGANISM: Rattus norvegicus

<400> SEQUENCE: 8

Gly Asp Ser Leu
1

<210> SEQ ID NO 9
<211> LENGTH: 19
<212> TYPE: PRT
<213> ORGANISM: Homo sapiens

<400> SEQUENCE: 9

Ser Leu Pro Cys Asp Ile Cys Lys Asp Val Val Thr Ala Ala Gly Asp
1               5                   10                  15

Met Leu Lys

<210> SEQ ID NO 10
<211> LENGTH: 17
<212> TYPE: PRT

```
<213> ORGANISM: Homo sapiens

<400> SEQUENCE: 10

Ala Thr Glu Glu Glu Ile Leu Val Tyr Leu Glu Lys Thr Cys Asp Trp
1               5                   10                  15

Leu

<210> SEQ ID NO 11
<211> LENGTH: 27
<212> TYPE: PRT
<213> ORGANISM: Homo sapiens

<400> SEQUENCE: 11

Pro Asn Met Ser Ala Ser Cys Lys Glu Ile Val Asp Ser Tyr Leu Pro
1               5                   10                  15

Val Ile Leu Asp Ile Ile Lys Gly Glu Met Ser
            20                  25

<210> SEQ ID NO 12
<211> LENGTH: 8
<212> TYPE: PRT
<213> ORGANISM: Homo sapiens

<400> SEQUENCE: 12

Pro Gly Glu Val Cys Ser Ala Leu
1               5
```